US008129315B2

(12) United States Patent
Carell et al.

(10) Patent No.: US 8,129,315 B2
(45) Date of Patent: Mar. 6, 2012

(54) LABELLING STRATEGIES FOR THE SENSITIVE DETECTION OF ANALYTES

(75) Inventors: Thomas Carell, Krailling (DE); Anja Schwögler, Mannheim (DE); Glenn A. Burley, Leicester (GB); Johannes Gierlich, Frankfurt (DE); Mohammad Reza Mofid, Isfahan (IR)

(73) Assignee: Baseclick GmbH, Tutzing (DE)

( * ) Notice: Subject to any disclaimer, the term of this patent is extended or adjusted under 35 U.S.C. 154(b) by 524 days.

(21) Appl. No.: 11/913,156

(22) PCT Filed: Apr. 28, 2006

(86) PCT No.: PCT/EP2006/004017
§ 371 (c)(1),
(2), (4) Date: Dec. 23, 2008

(87) PCT Pub. No.: WO2006/117161
PCT Pub. Date: Nov. 9, 2006

(65) Prior Publication Data
US 2009/0215635 A1    Aug. 27, 2009

Related U.S. Application Data

(60) Provisional application No. 60/750,100, filed on Dec. 14, 2005, provisional application No. 60/676,785, filed on May 2, 2005.

(30) Foreign Application Priority Data

May 2, 2005   (EP) .................................... 05009618
Dec. 14, 2005 (EP) .................................... 05027370

(51) Int. Cl.
    C40B 40/08    (2006.01)
(52) U.S. Cl. .......... 506/16; 435/6.1; 536/22.1; 536/26.1
(58) Field of Classification Search .................. None
    See application file for complete search history.

(56) References Cited

U.S. PATENT DOCUMENTS

| 5,705,622 | A  | 1/1998  | McCapra |
|-----------|----|---------|---------|
| 6,737,236 | B1 | 5/2004  | Pieken et al. |
| 6,884,882 | B1 | 4/2005  | Kim et al. |
| 7,427,678 | B2 | 9/2008  | Pieken et al. |
| 2003/0171570 | A1 | 9/2003 | Schweitzer |
| 2003/0175728 | A1 | 9/2003 | Belousov et al. |
| 2005/0032081 | A1 | 2/2005 | Ju et al. |
| 2005/0260645 | A1* | 11/2005 | Green et al. ............ 435/6 |
| 2010/0081137 | A1 | 4/2010 | Carell et al. |

FOREIGN PATENT DOCUMENTS

| WO | WO 89/02475   | 3/1989  |
|----|---------------|---------|
| WO | WO 96/09316   | 3/1996  |
| WO | WO 96/34984   | 11/1996 |
| WO | WO 01/42505   | 6/2001  |
| WO | WO 03/079014  | 9/2003  |
| WO | WO 03/101972  | 12/2003 |
| WO | WO 2006/116629 | 11/2006 |
| WO | WO 2006/117161 | 11/2006 |
| WO | WO 2007/120192 | 10/2007 |

OTHER PUBLICATIONS

Held et al (2002 Nucleic Acids Research 30: 3857-3869).*
Lazrek et al (2001 Nucleosides & Nucleotides 17:1851-1856).*
Berthod, T. et al. "Synthesis and mass spectrometry analysis of oligonucleotides bearing 5- formyl1-2' —deoxyuridine in their structures". Nucleosides and Nucleotides 1996 United States, vol. 15, No. 7-8, 1996, pp. 1287-1305 XP002383615.
Kaoru Okamoto et al., "Synthesis of ara-cadeguomycin. 2-amino-3,4-dihydro-4-oxo-7-(beta-d-arabinofuranosyl)-7h_pyrrolo[2,3-d]pyrimidine-5-carboxylic acid". Bulletin of the Chemical Society of Japan, Chemical Society of Japan, Tokyo, JP, vol. 59, No. 6, Jun. 1, 1986, pp. 1915-1919 XP000601944.
Marsh Andrew J. et al. , "The synthesis and properties of oligoribonucleotide-spermine conjugates" Organic & Biomolecular Chemistry, Jul. 21, 2004, vol. 2, No. 14, pp. 2103-2112 XP002383616.
Kagel John R. et al. "A chemical model for the fragmentation reaction in thymidylate synthase catalysis: Synthesis and evaluation of a 5-methylene-1-(1,2,3,4-tetrahydroquinolyI)-6-allyluridine". Journal of Organic Chemistry, vol. 58, No. 10, 1993, pp. 2738-2746 XP002383617.
Riggins James et al. Kinetic and thermodynamic analysis of the hydrolytic ring-opening of the malondialdehyde-deoxyguanosine adduct, 3-(2'-deoxy-beta-D-erythro pentofuranosyl)-pyrimido[1,2-alpha]purin-10(3H)-one. Journal of the American Chemical Society. Jul. 7, 2004, vol. 126, No. 26, pp. 8237-8243, XP002383618.
Minakawa N. et al., "A versatile modification of on-column oligodeoxynucleotides using a copper-catalyzed oxidative acetylenic coupling reaction". Journal of the American Chemical Society, Sep. 24, 2003, vol. 125, No. 38, pp. 11545-44552, XP002383619.
Lee Lac V. et al. "A potent and highly selective inhibitor of human alpha-1,3-fucosyltransferase via click chemistry". Journal of the American Chemical Society, vol. 125, No. 32, Aug. 13, 2003, pp. 9588-6589, XP002383611.
Byum Youngjoo et al. "Synthesis and biological evaluation of neutral and zwitterionic 3-carboranyl thymidine analogues for boron neutron capture therapy". Journal of Medicinal Chemistry, vol. 48, No. 4, Feb. 24, 2005, pp. 1188-1198, XP002383612.
Higashiya S. et al. "A facile synthesis of 2-azidoadenosine derivatives from guanosine as photoaffinity probes". Bioorganic & Medicinal Chemistry Letters, Oxford, GB, vol. 6, No. 1, 9 Jan. 1996, pp. 39-42, XP004135119.
Nam N-H et al. "ATP-phosphopeptide conjugates as inhibitors of src tyrosine kinases". Bioorganic and Medicinal Chemistry, Elsevier Science Ltd, GB, vol. 12, No. 22, Nov. 15, 2004, pp. 5753-5766, XP 004604949.
Hyde Robyn M. et al., "Antiviral amphipathic oligo- and polyribonulcleotides: Analogue development and biological studies". Journal of Medicinal Chemistry, vol. 46, No. 10, May 8, 2003, pp. 1878-1885, XP002383613.

(Continued)

Primary Examiner — Christopher M. Gross
(74) Attorney, Agent, or Firm — Brinks Hofer Gilson & Lione

(57) ABSTRACT

The present invention relates to methods and reagents for detecting analytes, e.g. nucleic acids. The new methods and reagents allow a simple and sensitive detection even in complex biological samples.

40 Claims, 29 Drawing Sheets

OTHER PUBLICATIONS

Buff R. et al. "Z-dna formation by 2'-C-ethynyl-modified oligonucleotides". Synlett 1999 Germany, No. SPEC. ISS, 1999, pp. 905-908, XP002383614.

Burley G et al. "Directed DNA metallization". Journal of the American Chemistry Society, vol. 128, No. 5, Feb. 2006, pp. 1398-1399, XP002397907.

Burley G. et al. "New labeling strategies for the sensitive detection of nucleic acids". Chemistry of Nucleic and Acid Components Acad Sci Czech Republic, Inst Organic Chem. & Biochemistry, Felingovoniam 2, Prague 166106, Czech Republic Series: Collection Symposium Series, 2005, pp. 229-232, XP008068569 & 13$^{th}$Symposium on Chemistry Nucleic Acid Components; Spindleruv Mlyn, Czech Republic; Sep. 2005.

Extended European Search Report for EP Application No. 10171618. 1, Completion Date: Sep. 30, 2010; Mailing Date: Nov. 9, 2010.

Martin, R. et al., "A highly sensitive, nonradioactive DNA labeling and detection system", Biotechniques, Natick, MA, US; 9(6), (1990), 762-766. XP000606333.

Matsuo, T., "In situ visualization of messenger RNA for basic fibroblast growth factor in living cells", Biochimica et Biophysica Acta, 1379 (2), (1998), 178-184. XP002602819.

Santangelo, P. et al., "Dual FRET molecular beacons for mRNA detection in living cells", Nucleic Acids Research, 32(6), (2004), 1-9. XP002602820.

Berthod, T. et al. "Synthesis and mass spectrometry analysis of oligonucleotides bearing 5- formyl1-2' —deoxyuridine in their structures". Nucleosides and Nucleotides 1996 United States, vol. 15, No. 7-8, 1996, pp. 1287-1305 XP002383615.

International Preliminary Report on Patentability for International Application No. PCT/EP2006/004017 and European Search Report, 1997.

Kolb H.C. et al.: Click Chemistry: Diverse chemical function from a few good reactions, Angewandte Chemie, International Edition, vol. 40, 2001, pp. 2004-2021, XP 001206265.

Sivakumar K. et al.: A fluorogenic 1,3-dipolar cycloaddition reaction of 3-azidocoumarins and acetylenes, Organic Letters, vol. 6, No. 24, 2004, pp. 4603-4606, XP 002995168.

Kolb H.C., Sharpless K.B,: The growing impact of click chemistry on drug discovery, Drug Discovery Today, vol. 8, No. 24, Dec. 15, 2003, pp. 1128-1137, XP 002377521.

Seo Tae Seok et al.: Click chemistry to construct fluorescent oligonucleotides for DNA sequencing, Journal of Organic Chemistry, vol. 68, No. 2, Dec. 21, 2002, pp. 609-612, XP 0022387640.

Deiters A., Schultz P.G.: In vivo incorporation of an alkyne into proteins in *Escherichia coli*, Bioorganic & Medicinal Chemistry Letters, vol. 15, No. 5, Mar. 1, 2005, pp. 1521-1524, XP 004750702.

Trevisiol E. et al.: The oxyamino-aldehyde coupling reaction: An efficient method for the derivatization of oligonucleotides, Tetrahydron Letters, vol. 38, No. 50, 1997, pp. 8687-8690.

Nguyen H-K et al.: Studies towards the design of a modified GC base pair with stability similar to that of the AT base pair, Tetrahydron Letters, vol. 38, No. 23, 1997, pp. 4083-4086, XP 002041345.

Venyaminova A G et al: New photoreactive mRNA analogues for the affinity labeling of ribosomes, Nucleosides and Nucleotodes, vol. 14, No. 3-5, 1995, pp. 1069-1072.

Extended European Search Report for European Application No. 10 17 1611, dated Oct. 13, 2010.

Dobrikov et al., "Sensitized photomodification of DNA by binary system of oligonucleotide conjugates. III. Two-photon sensitization", Bioorganics, 1998, 24:11, 831-838.

Malakhov et al., "Synthesis of a new fluorescent 9,10-bisphenylethynylanthracene-derived pseudonucleoside and its introduction into oligonucleotides", Bioorganics, 1999, 25:12, 933-937.

Russian Office Action dated Sep. 15, 2009, RU Application No. 2007 144 529.

Wang Q. et al.: "Bioconjugation by Cooper(I)-Catalyzed Azide-Alkyne [3+2] Cycloaddition." Journal of the American Chemical Society, vol. 125, No. 11, Mar. 9, 2003, pp. 3192-3193, XP008128703.

Lin H. et al.: "A Chemoenzymatic Approach to Glycopeptide Antibiotics." Journal of the Americann Chemical Society, vol. 126, No. 43, 2004, pp. 13998-14003, XP002632941.

Extended European Search Report for EP Application No. 10177873. 6, Completion Date: Apr. 14, 2011, Mailing Date: May 16, 2011.

De Clercq, E. et al., "(*E*)-5-(2-Bromovinyl)-2'-deoxyuridine: A potent and selective anti-herpes agent", Proc. Natl. Acad. Sci., vol. 76, No. 6, Jun. 1979, pp. 2947-2951.

Otvos, L., et al., "Base Modified Oligodeoxynucleotides. II. Increase of Stability to Nucleases by 5-Alkyl-, 5-(1-Alkenyl)-, and 5-(1-Alkynyl)-pyrimidines", Nucleosides, Nucleotides and Nucleic Acids, vol. 18, No. 9, 1999, pp. 1929-1933.

Burley, G. et al., "Directed DNA Metallization" J. Am. Chem. Soc. 2006, 128, 1398-1399 and S1-S21.

Fischler, M. et al., "Chain-like assembly of gold nanoparticles on artificial DNA templates via 'click chemistry'", Chem. Commun., 2008, 169-171.

Fischler, M. et al., "Formation of Bimetallic Ag-Au Nanowires by Metallization of Artificial DNA Duplexes" Small, 2007, 3, No. 6, 1049-1055.

Gierlich, J. et al., "Synthesis of Highly Modified DNA by a Combination of PCR with Alkyne-Bearing Triphosphates and Click Chemistry" Chem. Eur. J., 2007, 13, 9486-9494 and S1-S27.

Gramlich, P.M.E. et al., "Synthesis of Modified DNA by PCR with Alkyne-Bearing Purines Followed by a Click Reaction", Org. Lett., 2008, 10, No. 2, 249-251 and S1-S16.

Wirges, C.T. et al., "Pronounced Effect of DNA Hybridization on Click Reaction Efficiency" QSAR Comb. Sci. 26, 2007, No. 11-12, 1159-1164.

Aucagne Vincent et al.: "Chemoselective formation of successive triazole linkages linkages in one pot: "click-click" chemistry." Organic Letters, vol. 8, No. 20, 28 Sep. 2006, pp. 4505-4507; XPOO0910784.

Baruch Amos et al.: "Enzyme activity: It's all about image." Trends in Cell Biology, Elsevier Science LTD, vol. 14, No. 1, Jan. 1, 2004, pp. 29-35, XP002309365.

Fischer Rainer et al.: "A targeted protease substrate for a quantitative determination of protease activities in the endolysosomal pathway." Chembiochem Wiley VCH, Weinheim, DE, vol. 7, No. 9, Sep. 1, 2006, pp. 1428-1434, XP002442P94.

Geci I. et al.: "Synthesis of twisted intercalating nucleic acids possessing acridine derivatives. Thermal stability studies." Bioconjugate Chemistry, ACS, Washington, DC, US, vol. 17, No. 4, Jun. 21, 2006, pp. 950-957, XP002399203.

Gierlich Johannes et al.: "'Click' chemistry as a reliable method for the high-density postsynthetic functionalization of alkyne-modified DNA." Organic Letters, vol. 8, No. 17, Aug. 17, 2006, pp. 3639-3642, XP009107846.

Jang Hangjun et al.: "Click to fit: versatile polyvalent display on a peptidomimetic scaffold." Organic Letters, vol. 7, No. 10, May 12, 2005, pp. 1951-1954, XP000910778.

Kolb H.C. et al.: -"The growing impact of click chemistry on drug discovery." Drug Discovery Today, Elsevier, Rahway, NJ, US, vol. 8, .No. 24, Dec. 15, 2003, pp. 1128-1137, XP002377521.

Lu Genliang et al.: "An iterative route to "decorated" ethylene glycol-based linkers." Chemical Communications (Cambridge, England), No. 15, Apr. 21, 2006, pp. 1652-1654, XP009107801.

Montagnat et al.: "Synthesis of azide-alkyne fragments for 'click' chemical applications; formation of oligomers from orthogonally protected trialkylsilyl-propargyl azides and propargyl alcohols" Tetrahedron Letters, Elsevier, Amsterdam, vol. 47, No. 39, Sep. 25, 2006, pp. 6971-6974, XP005614805.

Sieber Stephan A et al.: "Proteomic profiling of metalloprotease activities with cocktails of active-site probes." Nature Chemical Biology, vol. 2, No. 5, May 2006, pp. 274-281, XPOQ9107764.

Speers A et al.: "Profiling enzyme activities in vivo using click chemistry methods." Chemistry and Biology, Current Biology, London, GB, vol. 11, No. 4, Apr. 1, 2004, pp. 535-546, XP00237Z550.

Speers Anna E et al: "A tandem orthogonal proteolysis strategy for high-content chemical proteomics." Journal or the American Chemical Society, vol. 127, No. 28, Jul. 20, 2005, pp. 10018-10019, XP009107850.

Ustinov Av et al: "Oligonucleotides containing aryl acetylene residues: Synthesis and post-synthetic modification via [3+2] cycloaddition" Russian Chemical Bulletin, Kluwer Academic Publishers—Plenum Publishers, NE, vol. 55, No. 7, Jul. 1, 2006, pp. 1268-1274. XP019454004.

\* cited by examiner 7-dN-G<sup>mod</sup>    C<sup>mod</sup>    7-dN-A<sup>mod</sup>    T<sup>mod</sup>

Scheme 1

Dendrimer synthesis

The preparation of 9 [26] and the deprotected sugar [27] were reported previously.

Scheme 2

| Fluorescein Click | General staining with CYBR | Fluorescein Click | General staining with CYBR |
| A1 | A2 | B1 | B2 |

HPLC

Peak assignments:
9.5 min Cytidine
13.1 min Inosine (as a side product of snake venom)
13.6 min Guanosine
14.6 min Thymidine
16.7 min Adenosine
26.3 min. 7

Dilution series.

(a)

(b)

(c)

(d)

Natural DNA after exposing the DNA to the Ag staining conditions.

Sugar modified DNA

Sugar modified DNA after Ag staining without development

Sugar modified DNA after Ag staining and with 2 min of development

Sugar modified DNA after Ag staining and with two times 2 min of development (a) (b) (c)

(d) (e) (f)

(a)    (b)

ODN-4    ODN-5

LABELLING STRATEGIES FOR THE SENSITIVE DETECTION OF ANALYTES

This application is a National Stage application of International Application No. PCT/EP2006/004017 filed Apr. 28, 2006, which claims the benefit of U.S. Provisional Application No. 60/676,785 filed May 2, 2005; and U.S. Provisional Application No. 60/750,100 filed Dec. 14, 2005 the entire contents of which is hereby incorporated herein by reference. International Application No. PCT/EP2006/004017 also claims the benefit under 35 U.S.C. §119 of European Patent Application No. EP 05009618.9 filed May 2, 2005; and European Patent Application No. EP 05027370.5 filed Dec. 14, 2005.

The present invention relates to methods and reagents for detecting analytes, e.g. nucleic acids. The new methods and reagents allow a simple and sensitive detection even in complex biological samples.

BACKGROUND OF THE INVENTION

The rapid analysis of genetic material for specific target sequences, e.g. for the presence of single nucleotide polymorphisms, the presence of a certain gene, e.g. a resistance gene, or of mRNA requires easy to use, efficient and reliable new tools. The major problem is the need to detect the DNA or RNA of interest directly in small biological samples such as patient blood or plants. These provide the analyte only in minute amounts. In order to reach the required sensitivity an amplification step is usually required wherein either the nucleic acid analyte is amplified prior to analysis or a detection method is used in which the minute detection signal, directly obtained from the DNA/RNA analyte, is amplified.

Methods for the amplification of the nucleic acid analyte include PCR and other nucleic acid amplification protocols. PCR amplification has the major advantage that, within a pool of different DNA strands obtained from the biological material, only the DNA sequence of interest is amplified. This is the basis for the reliable analysis of single genes in complex biological samples. PCR amplification, however, requires complex process steps which, in some cases, are too inconvenient and expensive. Amplification of the detection signal may be achieved by binding an enzyme such a horse radish peroxidase to the analyte, which converts a given substrate continuously into a colored product.

DNA metallization is another way to amplify the detection signal. A single metallic particle attached to DNA/RNA (the nucleus) catalyzes the deposition of ever more metal, which catalyzes further metal deposition [1-9]. The signal induced by metal deposition grows accordingly in an exponential manner. The metal deposition can be detected either electrically, if the analyte is placed within two electrodes, or optically (e.g. with the eye) because the deposited metal gives rise to a black spot e.g. on paper, in the gel, or in the test tube. In principle, metal deposition is the most sensitive detection method because a small metal cluster (nucleus) is sufficient to start the reaction. In practice, however, the sensitivity of the method is limited by unspecific metal nucleation e.g. through impurities in close spatial vicinity to the analyte for example, on the electrodes, in the gel, or on the paper holding the analyte. In fact unspecific metal deposition is the major reason why silver staining of DNA is not routinely used in oligonucleotide analytics. Silver staining is further complicated by the fact that DNA is unable to build the initiation nucleus itself. It requires prior modification. The method of choice today is the reaction of DNA with glutaraldehyde which covalently attaches to the DNA by sequence-unspecific binding to primary amine groups on nucleobase [7]. This adduct, if treated with a silver salt, reduces the $Ag^+$ of the salt to atomic silver which, while bound to the DNA, functions as the required nucleus. Further treatment of the nucleated DNA with silver salts and reducing agents initiates the exponential metal deposition. Another possibility is to exchange the counterions on the DNA strand by $Ag^+$, which is subsequently reduced to give $Ag^0$ nucleation sites. The major disadvantage is that the glutaraldehyde also reacts with impurities or other chemical species close to the analyte, which again induces unspecific silver deposition.

Metal clusters such as Au, Pd particles or Pt-complexes attached to DNA also function as nucleation sites for further metal deposition up to the construction of conducting wires [1-9]. Here the clusters are attached to reactive groups which form a covalent bond with DNA or to units that just intercalate or bind otherwise to DNA/RNA. All these methods label the entire DNA in a biological sample and therefore do not allow sequence-specific marking and hence sequence-specific analysis of a target DNA such as a single gene in a complex biological sample.

The preparation of labelled DNA domains by a telomerase-mediated incorporation of amine-modified nucleoside triphosphates into a primer-initiated modified telomer repeat is described in [8]. The amine-containing telomers are functionalized with activated gold nanoparticle N-succinimidyl esters to yield gold nanoparticle DNA strands. Enlargement of these nanoparticle sites by further metal deposition along the DNA indeed yields rapid growth of the metal clusters up to the construction of DNA templated molecular nanowires. However, the efficiency of amine-modified triphosphate incorporation into the growing telomer end is low and requires triphosphate doping which results in a distribution of nucleation sites. Thus, the procedure does not allow sequence-specific labelling.

Site-specific labelling of DNA has also recently been attempted via a complex lithographic method [4]. According to this method, a partial protection of DNA molecules is effected by binding of RecA. The unprotected DNA sequences are then treated with glutaraldehyde which marks these sequences for metallization. Site-specific reduction of silver ions by the DNA-bound aldehyde functions results in wire formation along these regions. A sequence-specific labelling of nucleic acid molecules in a complex biological sample is not possible, however.

Although these documents demonstrate the interest in new labelling strategies of DNA, the complicated processes involved in order to achieve marking prevents these systems from being used for any real application. In particular, these methods are unable to selectively label DNA or RNA sequences of interest directly in a crude biological sample.

Thus it was an object of the present invention to provide novel methods and reagents which allow a simple, efficient and specific detection of analytes, particularly of nucleic acids in complex biological samples.

SUMMARY OF THE INVENTION

A first aspect of the present invention relates to methods and reagent kits for detecting an analyte, e.g. an analyte, e.g. a nucleic acid in a sample, wherein an association product of the analyte to be detected with a novel aldehyde-functionalized compound is formed, which allows sequence-specific detection by forming marker groups, e.g. metal depositions around aldehyde groups in said association product.

More particularly, an embodiment of this aspect relates to a method for detecting an analyte in a sample comprising the steps:
(i) providing a sample;
(ii) contacting the sample with a functionalized compound comprising at least one functional group selected from an aldehyde group, a protected aldehyde group, an aldehyde precursor group or a handle group for introducing an aldehyde group, a protected aldehyde group or an aldehyde precursor group, under conditions wherein said compound forms an association product with the analyte to be detected;
(iii) if necessary, reacting the handle group with a reaction partner, comprising an aldehyde group, a protected aldehyde group or an aldehyde precursor group,
(iv) if necessary, converting protected aldehyde groups and aldehyde precursor groups to aldehyde groups,
(v) contacting said association product having aldehyde groups with a marker reagent under conditions wherein marker groups are formed around aldehyde groups in said association product, and
(vi) detecting said marker groups.

A further embodiment of this first aspect relates to a reagent kit for detecting an analyte in a sample, comprising:
(a) a functionalized compound comprising a functional group selected from an aldehyde group, a protected aldehyde group or an aldehyde precursor group, or a handle group for introducing an aldehyde group, a protected aldehyde group or an aldehyde precursor group,
(b) optionally a reaction partner for the handle group comprising an aldehyde group, a protected aldehyde group or an aldehyde precursor group,
(c) optionally an aldehyde-forming reagent capable of converting protected aldehyde groups and aldehyde precursor groups to aldehyde groups, and
(d) a marker reagent.

Still a further embodiment of this first aspect relates to a compound of formula (I):

wherein A is a functional group selected from an aldehyde group, a protected aldehyde group or an aldehyde precursor group,
S is a spacer or a bond, preferably a covalent bond, and
N is a nucleic acid or nucleic acid analogue building block such as a nucleosidic or nucleotidic compound.

In a second aspect the present invention relates to methods and reagent kits for detecting an analyte, e.g. a nucleic acid in a sample involving the use of a Click-functionalized compound which forms an association product with the analyte to be detected. The sequence-specific introduction of marker groups is effected by reacting the Click-functionalized compound with a suitable reaction partner comprising marker groups or marker precursor groups.

An embodiment of this second aspect relates to a method for detecting an analyte in a sample comprising the steps:
(i) providing a sample;
(ii) contacting the sample with a functionalized compound comprising at least one functional group which is a first reaction partner for a Click reaction under conditions wherein said compound forms an association product with the analyte to be detected,
(iii) contacting the association product with a second reaction partner for a Click reaction under conditions wherein a Click reaction between the first and second reaction partner occurs, wherein the second reaction partner further comprises a marker group or a marker precursor group,
(iv) if necessary, converting marker precursor groups to marker groups, and
(v) detecting said marker groups.

A further embodiment of this second aspect relates to a reagent kit for detecting an analyte in a sample, comprising:
(a) a functionalized compound comprising at least one functional group which is a first reaction partner for a Click reaction,
(b) a second reaction partner for a Click reaction, wherein the second reaction partner further comprises a marker group or a marker precursor group, and
(c) optionally a marker forming reagent capable of converting marker precursor groups to marker groups.

Still a further embodiment of this second aspect relates to a compound of the formula (II):

wherein C is a functional group which is a first reaction partner for a Click reaction,
S is a spacer or a bond, preferably a covalent bond and
N is a nucleic acid or nucleic acid analogue building block such as a nucleosidic or nucleotidic compound.

In a third aspect the present invention relates to methods and reagent kits for detecting an analyte, e.g. a nucleic acid in a sample involving the use of a photosensitizer compound which forms an association product with the analyte to be detected. Preferably, photosensitizer groups are sequence-specifically introduced into a nucleic acid. The presence of photosensitizer groups is detected by irradiating the labelled association product in contact with a photosensitive medium, wherein the presence of photosensitizer groups selectively causes a site-specific formation of marker groups in the marker medium.

An embodiment of this third aspect relates to a method for detecting an analyte in a sample by forming an association product of the analyte and a functionalized compound comprising photosensitizer groups and effecting an energy transfer, particularly a transfer of radiation energy from the photosensitizer groups to a photosensitive medium wherein the energy transfer causes selective formation of marker groups in the photosensitive medium.

A further embodiment of this third aspect relates to a method for detecting an analyte in a sample comprising the steps:
(i) providing a sample;
(ii) contacting the sample with a functionalized compound comprising at least one functional group selected from a photosensitizer group or a handle group for introducing a photosensitizer group under conditions wherein said compound forms an association product with the analyte to be detected;
(iii) if necessary, reacting the handle group with a reaction partner comprising a photosensitizer group;
(iv) irradiating said association product in contact with a photosensitive medium under conditions wherein marker groups are formed in said photosensitive medium in the presence of photosensitizer groups in said association product, and
(v) detecting said marker groups.

Still a further embodiment of this third aspect relates to a reagent kit for detecting an analyte in a sample, comprising:
(a) a functionalized compound comprising at least one functional group selected from a photosensitizer group or a handle group for introducing a photosensitizer group;
(b) optionally a reaction partner for the handle group comprising a photosensitizer group, and;
(c) a photosensitive medium which forms marker groups upon irradiation in the presence of photosensitizer groups.

The present invention allows a highly sensitive detection of an analyte, e.g. nucleic acids or nucleic acid binding proteins, in biological samples, e.g. clinical samples, environmental samples or agricultural samples. Preferred applications include, but are not limited to, the detection of genetic variabilities, e.g. single nucleotide polymorphisms (SNPs), pesticide or medicament resistances, tolerances or intolerances, genotyping, e.g. the detection of species or strains of organisms, the detection of genetically modified organisms or strains, or the detection of pathogens or pests, and the diagnosis of diseases, e.g. genetic diseases, allergic diseases, autoimmune diseases or infectious diseases. A further preferred application is the detection of nucleic acids in samples for brand protection, wherein products such agricultural products, food products, or goods of value and/or packaging of these products are encoded with product-specific information, e.g. but not limited to production site, date production, distributor etc., and wherein this information is detected with the methods as described above.

DETAILED DESCRIPTION OF PREFERRED EMBODIMENTS

The invention provides methods and reagents that allow specific labelling of analytes with marker groups, e.g. with reactive aldehyde groups in a complex sample. In a preferred embodiment, metal deposition, e.g. silver deposition, can be effected specifically on the aldehyde groups associated with the nucleic acid to be detected. In a further preferred embodiment, metal deposition, e.g. silver deposition can be effected specifically by energy transfer from photosensitizing groups into a photosensitive medium, e.g. photographic paper. Due to the specific labelling procedure, the background is strongly reduced and higher sensitivities and reliabilities are obtained.

The present invention comprises the detection of an analyte. The detection may be a qualitative detection, e.g. the determination of the presence or absence of an analyte, e.g. a specific nucleic acid sequence in the sample to be analysed. The invention, however, also allows quantitative detection of an analyte, e.g. a nucleic acid sequence, in the sample to be analysed. Qualitative and/or quantitative detection may comprise the determination of labelling groups according to methods known in the art.

The analyte to be detected is preferably selected from nucleic acids and nucleoside-, nucleotide- or nucleic acid-binding molecules, e.g. nucleoside-, nucleotide- or nucleic acid-binding proteins. More preferably, the analyte is a nucleic acid, e.g. any type of nucleic acid which can be detected according to known techniques, particularly hybridization techniques. For example, nucleic acid analytes may be selected from DNA, e.g. double-stranded or single-stranded DNA, RNA, or DNA-RNA hybrids. Particular examples of nucleic acid analytes are genomic DNA, mRNA or products derived therefrom, e.g. cDNA.

The method of the invention can be carried out according to any known test format which is suitable for the detection of analytes, particularly nucleic acid analytes in a sample. For example, the method may involve the detection of analytes immobilized on solid surfaces such as membranes, e.g. in Southern or Northern blots, chips, arrays or particles such as beads. Further, the detection can be carried out in gels, e.g. after electrophoretic separation of the sample in gels, e.g. agarose or polyacrylamide gels. The method may involve the detection of single analytes or the parallel detection of a plurality of analytes, e.g. in a chip or microarray format.

In a preferred embodiment the detection involves irradiating a photosensitive medium in the presence of a sample containing an association product indicative for an analyte wherein the association product comprises photosensitizer groups capable of effecting an energy transfer to the photosensitive medium wherein marker groups are formed in the medium.

The sample may be any sample which may contain the analyte to be detected. For example, the sample may be a biological sample, such as an agricultural sample, e.g. a sample comprising plant material and/or material associated with the site where plants grow, plant materials are stored or processed. On the other hand, the sample may also be a clinical sample, such as a tissue sample or a body fluid sample such as blood, serum, plasma, etc, particularly of human origin. Further types of samples include, but are not limited to, environmental samples, soil samples, food samples, forensic samples or samples from valuable goods which are tested for brand protection.

Due to its high sensitivity, the method of the present invention is suitable for detecting analytes directly without amplification. According to the invention, even minute amounts of analytes, e.g. of nucleic acids, e.g. 0.1 ng or lower, preferably 0.01 ng or lower, more preferably 1 pg or lower, still more preferably 0.1 pg or lower, even more preferably 0.01 pg or lower and most preferably 0.001 pg or lower may be determined even without amplification. An especially high sensitivity may be obtained by incorporating multiple modified nucleotides into a nucleic acid molecule by using unprotected aldehyde groups and/or by using optimized staining techniques. For example, the detection of an analyte, e.g. a gene, in a biological sample, might be performed by a combination of Southern blotting and the inventive method. It should be noted, however, that the method of the present invention also allows the detection of nucleic acids combined with an amplification step, which may be carried out according to known protocols such as PCR or modifications thereof, such as asymmetric PCR, real-time PCR, reverse transcription PCR, etc. or other amplification protocols such as LCR.

In a preferred embodiment of the invention, a sequence-specific detection of the analyte is carried out, wherein for example a nucleic acid having a specific sequence is distinguished from other nucleic acid sequences in the sample or a polypeptide capable of binding a specific nucleic acid sequence is distinguished from other polypeptides in the sample. Such a sequence-specific detection preferably comprises a sequence-specific hybridization reaction by which the nucleic acid sequence to be detected is associated with a compound carrying a marker group or a marker precursor group. It should be noted, however, that the present invention also allows sequence-unspecific detection of nucleic acids, e.g. detection of any nucleic acids present in a sample.

In order to identify the analyte to be detected, the sample may be contacted with an aldehyde-functionalized, Click-functionalized or photosensitizer-functionalized compound under conditions wherein an association product with the analyte, e.g. a nucleic acid is formed. An aldehyde-functionalized compound comprises a functional group which may be an aldehyde group, a protected aldehyde group, an aldehyde precursor group, i.e. a group which may be converted to an aldehyde group without a significant detrimental effect on the detection procedure or a handle group for introducing an aldehyde group, a protected aldehyde group or an aldehyde precursor group.

The functionalized compound may comprise a single functional group or a plurality of functional groups. For example, a functionalized compound may be coupled to a dendrimeric moiety comprising a plurality, e.g. 2, 3, 4, 5, 6, 7, 8 or more functional groups as indicated above. Dendrimeric moieties may be synthesized by known techniques. Preferably dendrimeric moieties are synthesized via Click reactions, e.g. as described in Example 5.

The functional group is attached to a compound which is capable of forming an association product with the analyte. The compound may be a nucleosidic or nucleotidic compound, e.g. a nucleoside or nucleoside analogue or a nucleotide or nucleotide analogue or an oligomer or polymer comprising at least one functionalized compound, e.g. a nucleic acid or nucleic acid analogue. A nucleosidic or nucleotidic compound is a nucleoside or nucleotide analogue or a nucleotide or nucleotide analogue capable of being incorporated into nucleic acids or nucleic acid analogues, e.g. by chemical or enzymatic methods. The resulting nucleic acid or nucleic analogue should be capable of forming association products, e.g. nucleic acid hybrids, with the analyte. Preferably, the compound comprises a base moiety, e.g. a nucleobase or another heterocyclic base moiety capable of forming base pairs with a nucleobase, and a backbone moiety, e.g. comprising a sugar moiety and optionally a phosphate moiety in nucleosides or nucleotides or a different backbone moiety in nucleoside or nucleotide analogues.

Preferred examples of functional nucleosidic compounds, wherein the nucleobase is 7-dN-G, C, 7-dN-A or T, and R is a functional group are shown in FIG. 1.

Preferably, the functional group is attached to a base moiety, e.g. to a nucleobase. The functional group, however, may also be attached to a backbone moiety, e.g. a sugar group, a phosphate group or, in the case of nucleoside or nucleotide analogues, a modified sugar group, a modified phosphate group or peptide backbone moiety, etc. Preferably, the functional group is covalently attached to the compound via a direct bond or via a spacer. If the attachment is effected via a spacer, the functional group may be linked to an aliphatic or cycloaliphatic group, an aromatic or heteroaromatic group, an alkene group and/or an alkyne group. More preferably, the functional group may be linked to aromatic or heteroaromatic groups or to alkyne groups. Especially preferred aldehyde groups include aromatic and aliphatic aldehyde groups such as benzaldehyde, or aldehyde groups in aldoses such as trioses, tetroses, pentoses or hexoses like glucose or mannose.

The functional group may be a free aldehyde group. The functional group may also be a protected aldehyde group, i.e. group which may be converted under the assay conditions to an aldehyde group. A preferred protected aldehyde group is an acetal or hemiacetal group which can be converted into a free aldehyde group by treatment with acids, e.g. organic or inorganic acids. Preferred examples of acetal or hemiacetal groups are acetal groups formed with a polyalcohol such as propane diol or ethylene glycol, or hemiacetal groups in a sugar or in a sugar-related compound such as an aldose sugar, e.g. glucose or galactose. Further examples of protected aldehyde groups are imino groups (e.g. =NH groups), which give aldehyde groups upon treatment with acids, thioacetal or dithioacetal groups (e.g. C (SR)$_2$ groups wherein R may be an alkyl radical) which give aldehyde groups upon treatment with mercury salts, oxime groups (e.g. =NOH groups), which give aldehyde groups upon treatment with acids, hydrazone groups (e.g. =N—NHR groups wherein R may be an alkyl radical) which give aldehyde groups upon treatment with acids and imidazolone or imidazolidine groups or benzothiazole or dihydrobenzothiazole groups which give aldehydes upon hydrolysis, e.g. with acid. Specific examples of functionalized compounds comprising free or protected aldehyde groups and methods for preparing such compounds are shown in FIGS. 2, 3a, 3c, 7, 8, 9d, and 9e.

The functional group may also be an aldehyde precursor group, i.e. a group which may be converted to an aldehyde group without a significant detrimental effect on the nucleic acid detection procedure. Preferred aldehyde precursor groups may be selected from carboxylic acids and carboxylic acid derivatives including nitriles which give aldehydes upon reduction and primary alcohols which give aldehydes upon oxidation.

In a different embodiment, the functional group may be a photosensitizer group, i.e. a group which is capable of effecting an energy transfer, e.g. a transfer of light energy, to a photosensitive medium, i.e. a photographic medium such as photographic paper. The photosensitizer groups may be selected from known fluorescent and/or dye labelling groups such as cyanine-based indoline groups, quinoline groups, for example commercially available fluorescent groups such as Cy5 or Cy5.5. Specific examples of photosensitizer groups are shown in FIG. 22.

The functional group may also be a handle group, i.e. a group for introducing an aldehyde group, a protected aldehyde group or an aldehyde precursor group or for introducing a photosensitizer group by reaction with a suitable reaction partner, i.e. a compound comprising one of the above groups. In a preferred embodiment, the handle groups are selected from Click functionalized groups, i.e. groups which may react with a suitable reaction partner in a cycloaddition reaction wherein a cyclic, e.g. heterocyclic linkage between the Click functional group and the reaction partner is formed, and wherein the reaction partner comprises an aldehyde or a protected aldehyde group or a photosensitizer group. An especially preferred example of such a Click reaction is a (3+2) cycloaddition between azide and alkyne groups which results in the formation of 1,2,3-triazole rings. Thus, aldehyde groups, may be generated by performing a Click reaction of an azide or alkyne handle group and a corresponding reaction partner, i.e. a reaction partner comprising the complementary alkyne or azide group and additionally an aldehyde, a protected aldehyde group or an aldehyde precursor. In a further embodiment of the invention, the reaction partner of the Click-functionalization, however, may also contain different marker or marker precursor groups such as fluorescence marker groups or photosensitizer groups.

An especially preferred embodiment of the Click reaction comprises a copper catalyzed (3+2) cycloaddition between an azide and an alkyne group. The irreversible formation of 1,2,3-triazoles as a result of the azide/alkyne cycloaddition is orthogonal, the required chemical groups are small (incorporation with minimal disruption of the biomolecule's environment) and selective due to the lack of azides and alkynes found in nature.

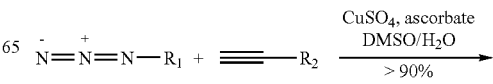

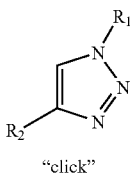

"click"

wherein $R_1$ and $R_2$ are organic-radicals.

Specific examples of Click-functionalized compounds and methods for preparing such compounds are shown in FIGS. 3b, 9a-c and 10. Specific examples of reaction partners for Click-functionalized compounds are shown in FIGS. 11 and 12.

The functional group, e.g. an aldehyde-functionalized group or a Click-functionalized group or a photosensitizer-functionalized group is preferably attached to a nucleobase which may be selected from naturally occurring and non-naturally occurring purine and pyrimidine bases. Preferably, the nucleobases are selected from cytidine, uracil, thymine, adenine, guanine, 7-deazaadenine, 7-deazaguanine, inosine and xanthine. The functional group is preferably attached to position 5 or 6, more preferably to position 5, of a pyrimidine nucleobase or to position 7 or 8, more preferably to position 7 of a purine nucleobase, particularly if an enzymatic incorporation into a nucleic acid is desired.

The functional group may be covalently attached to the compound, e.g. via a direct bond or a spacer, e.g. a spacer having a chain length up to 20 atoms. The spacer may be a flexible spacer, e.g. an alkylene-based spacer, optionally containing heteroatoms such as O, S, and/or N or an at least partially rigid spacer, e.g. a spacer which comprises at least one rigid group selected from alkene groups, alkyne groups, cyclic groups, particularly aromatic or heteroaromatic groups, but also cycloaliphatic groups and combinations thereof. If the functionalization compound comprises a Click-functionalization group which is the first reaction partner for a Click-reaction and subsequently reacted with a second reaction partner for a Click-reaction, an attachment of the functional group via a direct bond, a flexible spacer or an partially rigid spacer is preferred wherein the flexible spacer could for example have a chain length up to 6 atoms, more particularly up to 4 atoms, and wherein a partially rigid spacer preferably has a chain length of up to 20 atoms, e.g. up to 10 atoms and comprises at least one rigid group as defined above, particularly an alkyne group, and at least one flexible group, e.g. an alkylene group. If on the other hand, the functional group is an aldehyde group or a protected aldehyde group or an aldehyde precursor group attachment via or a partially rigid spacer as defined above or an at least partially rigid spacer having a chain length of from 2 to 10 atoms is preferred. The structure of a rigid group-containing spacer, e.g. a partially rigid spacer, is preferably such that the rigid group is directly attached to the nucleobase. A preferred example of a partially rigid spacer is shown in FIGS. 15a and b.

The functionalized compound is capable of forming an association product with the analyte to be detected. On the one hand, the functionalized compound may be selected from compounds which can be incorporated into nucleic acids or nucleic acid analogues, i.e. nucleic acid or nucleic acid analogue building blocks. Preferred examples for such compounds are nucleotides or nucleotide analogues, e.g. aldehyde-functionalized nucleotides or nucleotide analogues, Click-functionalized nucleotides or nucleotide analogues or photosensitizer-functionalized nucleotides or nucleotide analogues. On the other hand, the functionalized compound may be selected from nucleic acids or nucleic acid analogues, e.g. aldehyde-functionalized nucleic acids or nucleic acid analogues, Click-functionalized nucleic acids or analogues or photosensitizer-functionalized nucleic acids or analogues.

The term "nucleotide" according to the present invention particularly relates to ribonucleotides, 2'-deoxyribonucleotides or 2'; 3'-dideoxyribonucleotides. Nucleotide analogues may be selected from sugar- or backbone modified nucleotides, particularly of nucleotide analogs which can be enzymatically incorporated into nucleic acids. In preferred sugar-modified nucleotides the 2'-OH or H-group of the ribose sugar is replaced by a group selected from OR, R, halo, SH, SR, $NH_2$, NHR, $NR_2$ or CN, wherein R is $C_1$-$C_6$ alkyl, alkenyl or alkynyl and halo is F, Cl, Br or I. The ribose itself can be replaced by other carbocyclic or heterocyclic 5- or 6-membered groups such as a cyclopentane or a cyclohexene group. In preferred backbone modified nucleotides the phospho(tri) ester group may be replaced by a modified group, e.g. by a phosphorothioate group or a H-phosphonate group. Further preferred nucleotide analogues include building blocks for the synthesis of nucleic acid analogs such as morpholino nucleic acids, peptide nucleic acids or locked nucleic acids.

Aldehyde-, Click- or photosensitizer-functionalized nucleic acids may be oligonucleotides, e.g. nucleic acids having a length of up to 30 nucleotide (or nucleotide analogue) building blocks or polynucleotides having a length or more than 30 nucleotide (or nucleotide analogue) building blocks. Preferably, the nucleic acids and nucleic analogues are capable of specific binding to the analyte, e.g. capable of hybridizing with a nucleic acid analyte under assay conditions. The minimum length is preferably 12 and more preferably 14 nucleotide (or nucleotide analogue) building blocks.

Functionalized nucleic acid or nucleic acid analogue building blocks may be incorporated into nucleic acids by standard techniques for chemical synthesis and/or by enzymatic incorporation. Chemical synthesis for example may be carried out by standard phosphoramidite chemistry using modified nucleoside phosphoramidites as building blocks in standard synthesis protocols. Other types of preferred building blocks for chemical synthesis include H-phosphonate or phosphorotriester modified nucleosides.

On the other hand, modified nucleotides may be incorporated into nucleic acids by enzymatic methods. Surprisingly, it was found that aldehyde- or Click-functionalized nucleoside triphosphates are accepted as enzyme substrates by nucleic acid synthesizing enzymes such as DNA polymerases, RNA polymerases, reverse transcriptases or telomerases. For example, it was found that modified nucleoside triphosphates are accepted by DNA polymerases commonly used for primer extension and amplification protocols, e.g. thermostable DNA polymerases such as Taq polymerase, Vent polymerase, Pfx polymerase, Pwo polymerase, or Therminator polymerase as described in Example 7. Enzymes accept modified triphosphates without loss in fidelity and allow a template-based incorporation into nucleic acids such as DNA and RNA.

The method of the present invention provides various embodiments of analyte detection. For example, functionalized nucleic acid building blocks, e.g. nucleotides or nucleotide analogues, together with appropriate enzymes, may be provided which are enzymatically incorporated into a nucleic acid molecule which forms the association product with the analyte. In the present invention, a single type of functionalized nucleotide or a plurality of different types of functionalized nucleotides may be employed. Alternatively or additionally, a functionalized nucleic acid or nucleic acid analogue may already be present, which has been manufactured, e.g. by chemical or enzymatic synthesis, and which specifically binds, e.g. by hybridization to the analyte to be detected.

In a preferred embodiment the method comprises a primer extension reaction optionally in combination with subsequent nucleic acid amplification steps such as PCR. For example, at least one primer molecule may be provided which hybridizes under assay conditions with a nucleic acid analyte to be detected or the complement thereof. The bound primer is then extended wherein a detectable extension product is obtained which is indicative for the presence and/or amount of the nucleic acid analyte to be detected. According to this embodiment, functionalized primers and/or functionalized nucleotides or nucleotide analogues for incorporation into the extension product may be used.

Alternatively and/or additionally the method of the invention may comprise the use of functionalized hybridization probes which hybridize under the assay conditions with the nucleic acid analyte to be detected or the complement thereof wherein the formation of a hybridization product is indicative for the presence and/or amount of the nucleic acid analyte to be detected.

The detection method of the invention may be carried out by any known nucleic acid detection protocols, e.g. involving the use of solid supports. For example, a solid support, e.g. a chip or array or a particulate material such as a bead may be provided to which a capture probe is bound capable of hybridizing to the analyte to be detected. The solid phase bound nucleic acid analyte may be detected by using functionalized hybridization probes which hybridize with the nucleic acid analyte in a different sequence part as the capture probe does and subsequent detection of the bound hybridization probe, e.g. with a metallization reagent. This method is particularly suitable for the diagnostic applications in the agricultural and clinical field, e.g. for the detection of DNA and/or mRNA from plants, e.g. genetically modified plants, DNA from pathogens or plant pests etc.

In a specific embodiment, the detection may involve contacting the association product of the analyte and a functionalized compound comprising a photosensitizer group with a photosensitive medium, e.g. by transferring a sample or sample aliquot in which an association product may be present onto the photosensitive medium, e.g. by spotting, pipetting etc. Upon irradiation, an energy transfer from the photosensitizer group to the photosensitive medium is effected such that marker groups such as metal, e.g. silver, nuclei are formed in the photosensitive medium in the presence, but not in the absence, of photosensitizer groups. If necessary, the marker groups may be subjected to a development procedure, e.g. a chemical or photochemical development procedure according to photographic techniques. The photosensitive medium may be any solid support or any supported material capable of forming marker groups, e.g. metal nuclei. Preferably, the photosensitive medium is a light sensitive medium, such as light sensitive paper or a light sensitive emulsion or gel on a supportive material. More preferably the photosensitive medium is a photographic medium such as photographic paper. Irradiation is carried out under conditions, e.g. of wavelengths and/or intensity of irradiation light, under which selective marker group formation takes place in the presence of photosensitizer groups. Preferably, irradiation takes place with infrared light and/or with long wave visible light, depending on the sensitivity of the medium. The irradiation wavelength may be e.g. 500 nm or higher, 520 nm or higher, 540 nm or higher, 560 nm or higher, 580 nm or higher for visible light or 700 nm to 10 μm, for infrared light.

An important aspect of the invention is the detection of genetic variabilities, e.g. single nucleotide polymorphisms (SNPs). The genome of, for example humans, contains nucleotide sequence variations at an average frequency of up to 0.1%. Therefore, these variabilities provide excellent markers for the identification of genetic factors contributing to complex disease susceptibility [16, 17]. Although there is a wide range of techniques available for the detection of SNPs, most of these methods are slow, require extensive instrumentation, and PCR amplification [18]. The present method, however, is both inexpensive and flexible enough to accommodate low, moderate and high-throughput screening needs with high speed, sensitivity and efficiency. Several possibilities exist to label selectively only the fully matching or the mismatching strands allowing to use the method of the invention for the detection of SNPs.

For example, the detection of nucleic acid matches or mismatches, e.g. in SNPs, may comprise the use of functionalized hybridization probes which hybridize under the assay conditions with the nucleic acid analyte to be detected for the complement thereof and subjecting the hybridization product to a treatment procedure wherein a hybridization product containing at least one mismatch is dissolved and wherein the presence of an undissolved hybridization product is indicative for the presence and/or amount of a nucleic acid which has a fully complementary sequence (i.e. no mismatch) to the hybridization probe.

The treatment for the dissolution of mismatch-containing hybridization products may comprise a mismatch digestion treatment, i.e. the use of mismatch detecting enzymes which cleave the hybridization product depending on the presence of a mismatch. Suitable enzymes for such a mismatch digestion treatment include mismatch-glycosylases such as those encoded by the genes hMSH2 and hMLH1 and Mut S, Mut L and Mut H. Additional proteins are MutY and Mig.Mthy1. Mig.Mthy1 cuts T out of a TG mismatch, MutY cuts out A in an AG mismatch and the enzyme TDG cuts out T in a TG mismatch.

Alternatively or additionally, mismatch-containing hybridization products may be dissolved by a differential hybridization treatment involving the adjustment of hybridization conditions, e.g. in view of temperature, salt concentration and/or washing with dimethyl ammonium chloride, wherein a mismatch containing hybridization product is dissolved and the fully complementary hybridization product remains stable.

In a still further embodiment, mismatches, e.g. SNPs, may be determined by enzyme-catalyzed selective primer elongation. For this purpose a primer is provided, wherein the 3' end of the primer is directly located upstream of a potential mismatch site on the template analyte. A primer extension is only possible when a nucleotide which is complementary to the next base on the template is present. By selecting a single type of functionalized nucleotide and determining whether it is incorporated into the primer or not, the base on the potential mismatch site can be determined.

The method of the invention comprises the detection of marker groups which are incorporated into an association product of the analyte with a functionalized compound. The marker groups are preferably selected from metal deposition-forming groups, e.g. aldehyde-functionalized groups, from fluorescent or fluorescence-forming groups or from redox active groups.

The formation of metal depositions requires the treatment of aldehyde groups with a metallization reagent, e.g. a reagent comprising metal atoms and/or ions selected from Ag, Au, Bi, Cu, Pd or Pt which can be selectively deposited around aldehyde groups, e.g. by reduction. Preferably, the metallization reagent comprises an $Ag^+$ salt such as an Ag-ammonium complex, i.e. the Tollens reagent. Further preferred examples of metallization reagents are Cu $(NO_3)/I_2$, platinum terpyridine complexes such as [Pt(terpy)Cl]Cl, $Pd(OAc)_2$ or $KAuCl_4$.

Further, the functionalized groups may also function as a handle to attach other marker groups such as fluorescent marker groups. For example, marker compounds with amino groups may be coupled to aldehyde groups by reductive amination in the presence of a reducing agent such as sodium cyanoborohydride. Alternatively hydrazone or oxime formation may be used to provide marker groups.

The detection of the marker groups may be carried out according to known methods. For example, metal depositions may be determined qualitatively and/or quantitatively by optical methods and/or electrical methods. In a preferred embodiment, metal depositions on a solid surface may be determined by measuring electrical parameters, e.g. conductivity. Fluorescent marker groups may be determined qualitatively and/or quantitatively by known fluorescent measurement methods, e.g. excitation via a suitable light source such as a laser and detecting the emitted fluorescent light.

In a further embodiment, the invention comprises the detection of marker groups which are site-specifically formed in a photosensitive medium in the presence of photosensitizer groups in an association product of the analyte with a functionalized compound. The photosensitizer groups are preferably selected from fluorescent or luminescent groups. The photosensitizer groups can be incorporated directly into the association product or via a handle, e.g. via a Click-reaction as explained above in detail. The photosensitive medium comprises groups which, when irradiated in the presence of photosensitizer groups, form detectable marker groups such as metal nuclei which can be developed according to standard photographic techniques, e.g. by chemical or photochemical development techniques.

The invention also relates to reagent kits for detecting analytes, e.g. nucleic acid analytes in a sample which comprise a functionalized compound having attached at least one functional group as described above. Generally, the kit may comprise a compound of formula (III)

F—S—N wherein F is any functional group as described above, e.g. a group A as defined in formula (I), a group C as defined in formula (II) and/or a photosensitizer group;

S is a spacer or a bond, preferably a covalent bond, and
N is a nucleic acid or nucleic acid analogue building block such as a nucleosidic or nucleotidic compound.

The reagent kit may optionally contain an aldehyde forming reagent or a second partner for a Click-reaction and marker or marker-forming reagents or a photosensitive medium. The kits are preferably used in a method as indicated above.

Further, the present invention relates to an aldehyde-functionalized compound of formula (I) or a Click-functionalized compound of formula (II) as indicated above. The functionalized compounds may be building blocks for the chemical or enzymatic synthesis of nucleic acids or nucleic acid analogues or precursors thereof. Preferably, the compounds are nucleoside triphosphates, particularly ribose, 2'-deoxyribose or 2'-, 3'-dideoxyribose nucleoside triphosphates or analogues thereof which may be enzymatically incorporated into nucleic acids.

Furthermore, the compounds may be building blocks for the chemical synthesis of nucleic acids, or nucleic acid analogues such as peptide nucleic acids, morpholino nucleic acids or locked nucleic acids. To this end nucleoside phosphoramidites, H-phosphonates, phosphotriesters or Fmoc and/or Boc protected nucleobase amino acids are suitable.

The invention also relates to a nucleic acid or nucleic acid analogue molecule having incorporated therein at least one compound of formula (I) and/or formula (II). The molecule may be a nucleic acid selected from DNA and RNA or a nucleic acid analogue, e.g. selected from peptidic nucleic acids, morpholino nucleic acids or locked nucleic acids as described in detail above.

Further, the invention relates to a method of synthesizing a nucleic acid or nucleic acid analogue molecule comprising incorporating at least one nucleotide or nucleotide analogue building block comprising a compound (I) and/or (II) into a nucleic acid or nucleic acid analogue molecule. The method may comprise a chemical synthesis and/or an enzymatic synthesis.

Furthermore, the invention relates to a metallization product of the nucleic acid or nucleic acid molecule as indicated above which is obtainable by treatment of an aldehyde functionalized compound containing nucleic acid with a metallization reagent as indicated in detail above.

Furthermore, the invention relates to an association product of the nucleic acid or nucleic acid analogue molecule as indicated above with an analyte as described above. Preferably, the association product is a hybridization product with a complementary nucleic acid.

In a preferred embodiment, the methods and the reagent kits of the present invention are used for agricultural applications. For example, the invention is suitable for the detection of nucleic acids from plants, plant pathogens or plant pests such as viruses, bacteria, fungi or insects. Further, the invention is suitable for detecting genetic variabilities, e.g. SNPs in plants or plant parts, plant pathogens or plant pests such as insects.

A further application is a detection or monitoring of herbicide, fungicide or pesticide resistances, tolerances or intolerances, e.g. resistances, tolerances or intolerances in fungi, insects or plants in organisms or populations of organisms. The invention is also suitable for rapid genotyping, e.g. for the rapid detection and/or differentiation of species or strains of fungi, insects, or plants. Further, detection and/or differentiation of genetically modified organisms for strains, e.g. organisms or strains of fungi, insects or plants is possible.

Due to the high sensitivity of the invention, early diagnostic of pathogens is possible, i.e. diagnostics before first symptoms of the presence of pathogens is visible. This is particularly important for the diagnosis of soy rust (Phakospora pachyrizi) or other pathogens, e.g. *Blumeria graminis, Septoria tritici* or *Oomycetes* or other pathogens for which control is only possible, if their presence is detected before it can be visually recognized.

Further, the invention is suitable for medical, diagnostic and forensic applications, e.g. in human or veterinary medicine, e.g. for the detection of nucleic acids from pathogens, e.g. human pathogens or pathogens of livestock or pet animals.

Further preferred applications include the detection of genetic variabilities, e.g. SNPs in humans or the detection of medicament resistances, tolerances or intolerances or allergies. Further, the invention is suitable for genotyping, particularly genotyping of humans in order to determine mutations associated with predisposition or enhanced risk of disorders, allergies and intolerances. The invention may also be used for detection of genetically modified organisms or strains, organisms or strains of bacteria or viruses but also genetically modified life stock animals etc. The invention is particularly suitable for the rapid diagnosis of diseases, e.g. genetic diseases, allergic diseases, autoimmune diseases or infectious diseases.

Furthermore, the invention is suitable for detecting the function and/or expression of genes, e.g. for research purposes.

Still a further embodiment is the use of the method for brand protection, e.g. for detecting specific information encoded in products such as valuable goods like plant protection products, pharmaceuticals, cosmetics and fine chemicals (e.g. vitamins and amino acids) and beverage products, fuel products, e.g. gasoline and diesel, consumer electronic appliances can be marked. Further, packaging of these and other products can be marked. The information is encoded by nucleic acids or nucleic acid analogues which have been incorporated into the product and/or into the packaging of a product. The information may relate to the identity of the manufacturer, to production sites, date of production and/or distributor. By means of the present invention, rapid detection of product-specific data can be carried out. A sample may be prepared from an aliquot of the product which is then contacted with one or several sequence-specific functionalized hybridization probes capable of detecting the presence of nucleic acid-encoded information in the sample.

The invention is also suitable for the field of nutrients. For example, in the feed area, animal nutrients, e.g. corn, are supplemented with a greater quantity of preservatives such as propionic acid. By applying the method of the invention, the addition of preservatives can be reduced. Further, genomic analysis with the method of the invention allows the prediction of an individual's capability to utilize specific nutrients (nutrigenomics).

Still a further preferred embodiment refers to the field of epigenetics. This embodiment particularly refers to an analysis of DNA, e.g. genomic DNA with regard to methylation of cytosine bases. In this embodiment, the DNA may be treated with a cytosine-specific reagent, e.g. hydrazine and/or hydroxylamine. By means of the treatment, a selective reaction of either cytosine or methylcytosine residues occurs. For example, treatment with hydroxylamine leads to a selective modification of cytosine residues. Preferably, the reagent is added in a sub-stoichiometric amount in order to obtain a partial modification of e.g. cytosine residues. Subsequently, the treated DNA is analysed, e.g. by a primer extension reaction using at least one modified nucleic acid building block as indicated above, e.g. a dU and/or dC base. Preferably a Click-modified base, e.g. an alkyne-modified base is used. The primer extension reaction gives a characteristic sequencing ladder resulting from interruptions of the reaction on the modified dC or 5-methyl-dC bases (cf. FIG. 26).

A further preferred embodiment refers to the application of reporter nucleic acid molecules to a photosensitive medium, e.g. photographic paper or any other light sensitive medium. Preferably, the reporter molecules carry a photosensitizer group and a quencher group. In the absence of analyte the photosensitizer group is quenched. For example, the reporter molecule may have a hairpin structure with the photosensitizer and the quencher group on or near the termini of the molecule in close spatial relation-ship. When the reporter molecule is present as a hairpin structure, the photosensitizer group is quenched (according to the known molecular beacon technique). Thus, a reporter molecule with an intact hairpin structure cannot effect a sensibilisation when irradiating light to the photosensitize medium. In the presence of an analyte the hairpin structure is broken up. The analyte may be a complementary nucleic acid strand or an enzyme which cleaves the hairpin structure or a protein which binds to the hairpin and thus brakes up the structure. The photosensitizer group is separated from the quencher group and thus is capable of photosensibilisation. In this case, irradiation of light leads to a sensibilisation of the photographic medium and thus to the detection of analyte (cf. FIG. 27).

In this embodiment the present invention relates to a method for detecting an analyte in a sample comprising the steps:
(i) providing a sample,
(ii) providing a reporter molecule comprising a photosensitizer group or a handle group for introducing a photosensitizer group and a quencher group wherein the photosensitizer group is quenched in the absence of the analyte to be detected,
(iii) contacting the sample with the reporter molecule under conditions wherein the quenching of the photosensitizer group is at least partially reduced or terminated in the presence of the analyte,
(iv) if necessary, reacting the handle group with a reaction partner comprising a photosensitizer group,
(v) irradiating said reporter molecule in contact with a photosensitive medium under conditions wherein marker groups are formed in said photosensitive medium in the presence of unquenched photosensitizer groups in said reporter molecule, and
(vi) detecting said marker groups Further, this embodiment refers to a reagent kit for detecting an analyte in a sample comprising
a) a reporter molecule comprising a photosentisitizer group or a handle group for introducing a photosensitizer group and a quencher group wherein the photosensitizer group is quenched in the absence of the analyte to be detected,
b) optionally a reaction partner for the handle group comprising a photosensitizer group and
c) a photosensitive medium which forms marker groups upon irradiation of unquenched photosensitizer groups Preferred aspects of the method an the reagent kits and preferred applications are as described above.

The invention is further explained by the following Figures and Examples.

Figure 1:
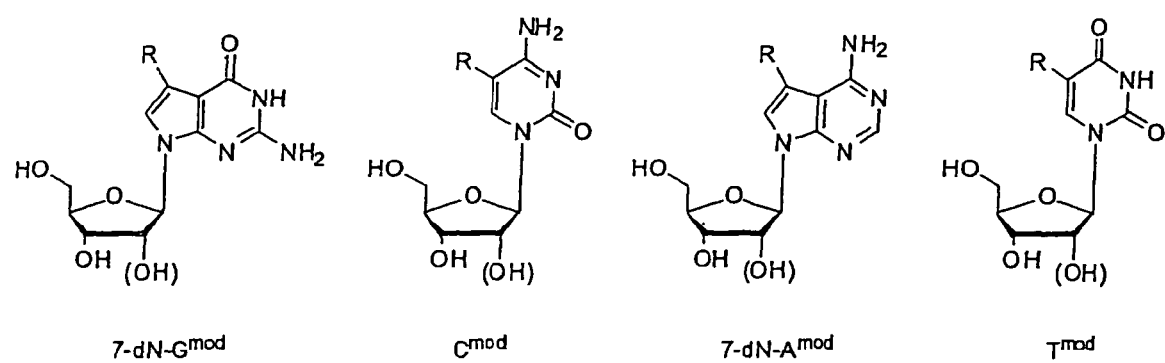
FIG. 1: Preferred attachment sites of functional groups (R), e.g. aldehyde functionalized groups on different nucleobases 7-dN-G, C, 7-dN-A and T for the enzymatic incorporation of marker groups into oligonucleotides.

(a) Dilution series of PCR fragments incorporating 1 (Lane 1 7.0 ng, Lane 2 3.5 ng, Lane 3 1.3 ng, Lane 4 0.7 ng) and 2 (Lane 5 7.0 ng, Lane 6 3.5 ng, Lane 7 1.3 ng, Lane 8 0.7 ng) run on a TBE-urea PMG gel. The gel was subjected to "on the gel" clicking with azide 3 and subsequent silver staining.

(b) Comparative detection of a dilution series of a PCR fragment incorporating 2 via (i) the selective silver staining method (as per (a)) and via (ii) SYBR green II (Lane 1 7 ng, Lane 2 3.5 ng, Lane 3 1.3 ng, Lane 4 0.9 ng, Lane 5 0.5 ng, Lane 6 0.3 ng). (c) Dilution series of PCR fragments incorporating 2 (Lane 1 7 ng, Lane 2 3.5 ng, Lane 3 1.3 ng, Lane 4 0.9 ng, Lane 5 0.5 ng, Lane 6 0.3 ng) and 2 Lane 1 7.0 ng, Lane 2 3.5 ng, Lane 3 1.3 ng, Lane 4 0.7 ng) run on TBE-urea PAAG gel. The gel was then subjected to "on the gel" clicking with aldehyde-modified azide 4 and subsequent silver staining. (d) Dilution series of PCR fragments incorporating 2 (Lane 1 7 ng, Lane 2 3.5 ng, Lane 3 1.3 ng, Lane 4 0.9 ng, Lane 5 0.5 ng, Lane 6 0.3 ng) run on TBE-urea PAAG gel. The gel was then subjected to "on the gel" clicking with aldehyde-modified azide 5 and subsequent silver staining.

FIG. 20: AFM photographs of natural DNA (a) and aldehyde-modified DNA (b) after exposure to Ag staining conditions, and aldehyde-modified DNA after Ag staining without development (c), after 2 min of development (d) and after two times 2 min of development (e).

Figure 21:
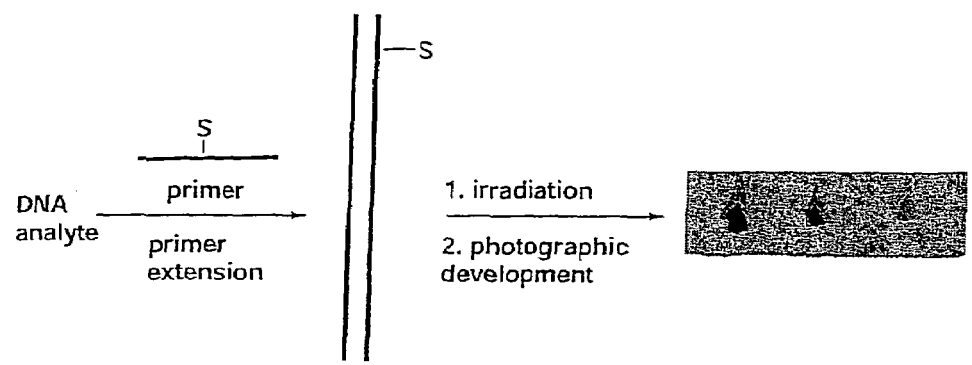

FIG. 21: A schematic depiction of an analyte, e.g. DNA analyte detection method using the principles of black and white photography. Initial replication of the DNA analyte in the presence of a sequence-selective primer produces a target sequence tagged with a sensitizer (S). After irradiation and subsequent photographic development the analyte can be detected on a photosensitive medium, e.g. photographic paper.

Figure 22:
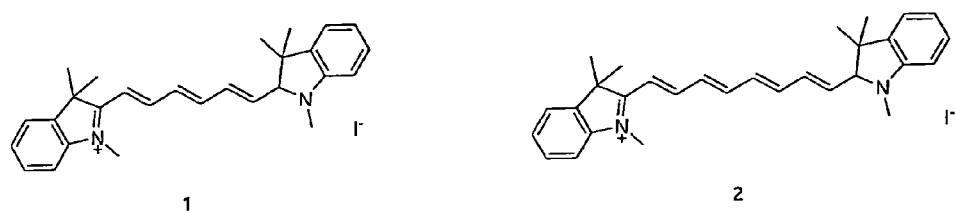
Figure 22:
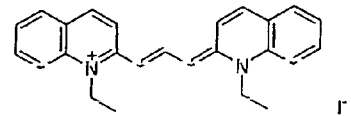
Figure 22:
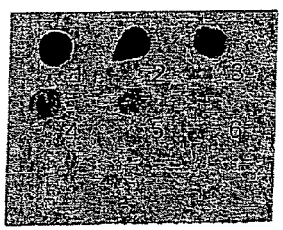
Figure 22:
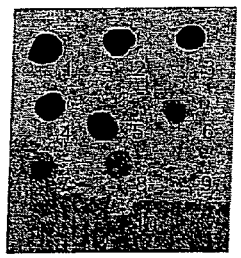
Figure 22:
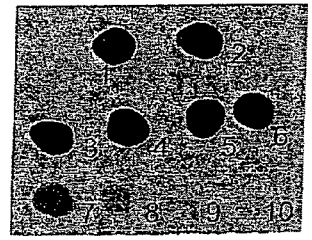
Figure 22:
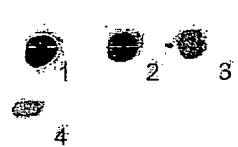
Figure 22:
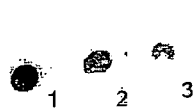
Figure 22:
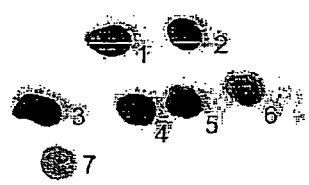

FIG. 22: Depiction of cyanine dyes (1), (2) and (3). Dilution series of cyanine dyes irradiated for 10 seconds using an overhead projector lamp equipped with a 520 nm cut-off filter using (a) 1; (b) 2; and (c) 3 or irradiation for 5 minutes with an infrared lamp using (d) 1, (e) 2 and f (3). The spot experiments correspond to the following dilutions: Spot $1:1\times10^{-1}$ mol., Spot 2: $1\times10^{-12}$ mol., Spot 3: $3\times10^{-13}$ mol, Spot 4: $1\times10^{-13}$ mol, Spot 5: $3\times10^{-14}$ mol, Spot 6: $1\times10^{-14}$ mol, Spot 7: $3\times10^{-15}$ mol, Spot 8: $1\times10^{-5}$ mol, Spot 9: $3\times10^{-16}$ mol, Spot 10: $1\times10^{-16}$ mol, FIG. 23: Spot tests of oligodeoxyribonucleotides ODN-1 [5'-GCG ATT CGT TCG TCG C-3'] (SEQ ID NO: 1), ODN-2 [5'-CGC GM TGA ACA GCG C-3'] (SEQ ID NO: 2) and ODN-3 [5'-GCG ACC GAT TCG C-3]' (SEQ ID NO: 3) all at 50 nmol using (a) high energy irradiation and a cut-off filter (520 nm); and (b) low energy irradiation via prolonged exposure (5 minutes) using an infrared lamp.

Figure 24:
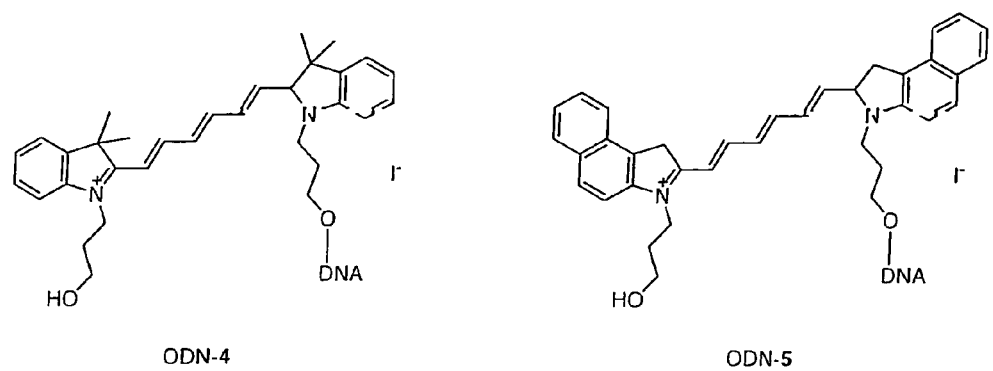
Figure 24:
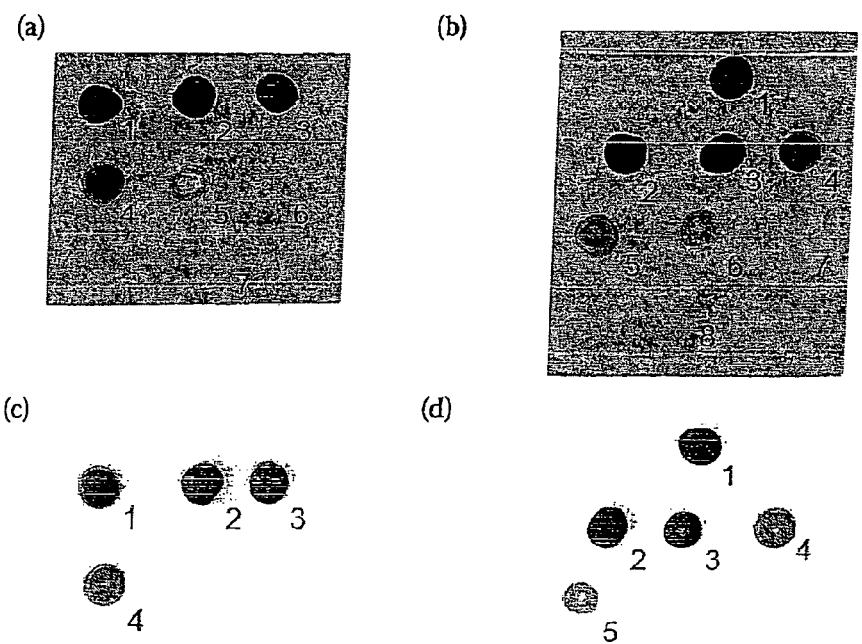

FIG. 24: Depiction of cyanine dyes Cy5 and Cy5.5. Dilution series of cyanine dyes tethered to ODNs irradiated for either 10 seconds using an overhead projector lamp equipped with a 520 nm cut-off filter using (a) ODN-4 [5'-Cy5-GCG CTG TTC ATT CGC G-3'] (SEQ ID NO: 4); (b) ODN-5 [5'-Cy5.5-GCG CTG TTC ATT CGC G-3'] (SEQ ID NO: 5); or irradiation for 5 minutes with an infrared lamp using (c) ODN4; (d) ODN-5. The spot experiments correspond to the following dilutions: Spot $1:1\times10^{-11}$ mol., Spot 2: $3\times10^{-12}$ mol., Spot 3: $1\times10^{-12}$ mol, Spot 4: $3\times10^{-13}$ mol, Spot 5: $1\times10^{-13}$ mol, Spot 6: $3\times10^{-14}$ mol, Spot 7: $1\times10^{-14}$ mol, Spot 8: $3\times10^{-15}$ mol.

Figure 25:
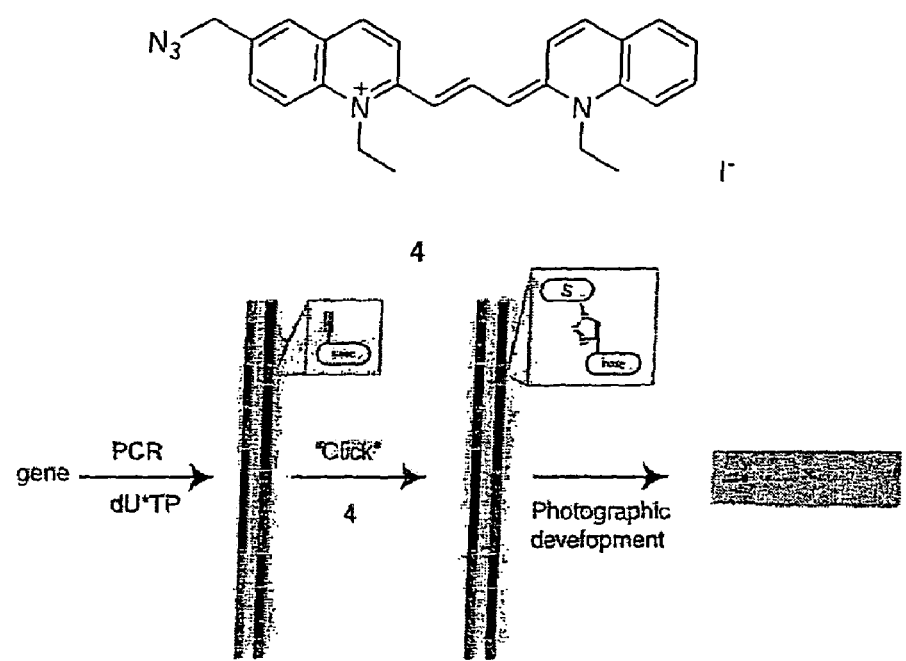

FIG. 25: Schematic depiction of the process of the "Click and photograph" methodology. A sequence, e.g. gene, of interest is specifically selected and amplified via PCR with alkyne-modified triphosphates (dU*TP) and gene-selective primers. These alkyne functions can be tagged via click chemistry with an appropriate photosensitizer (S) producing photosensitized DNA hybrids. Irradiation of the sample on photo paper and subsequent development will provide a new method for the ultra sensitive and specific detection of genes.

Figure 26:
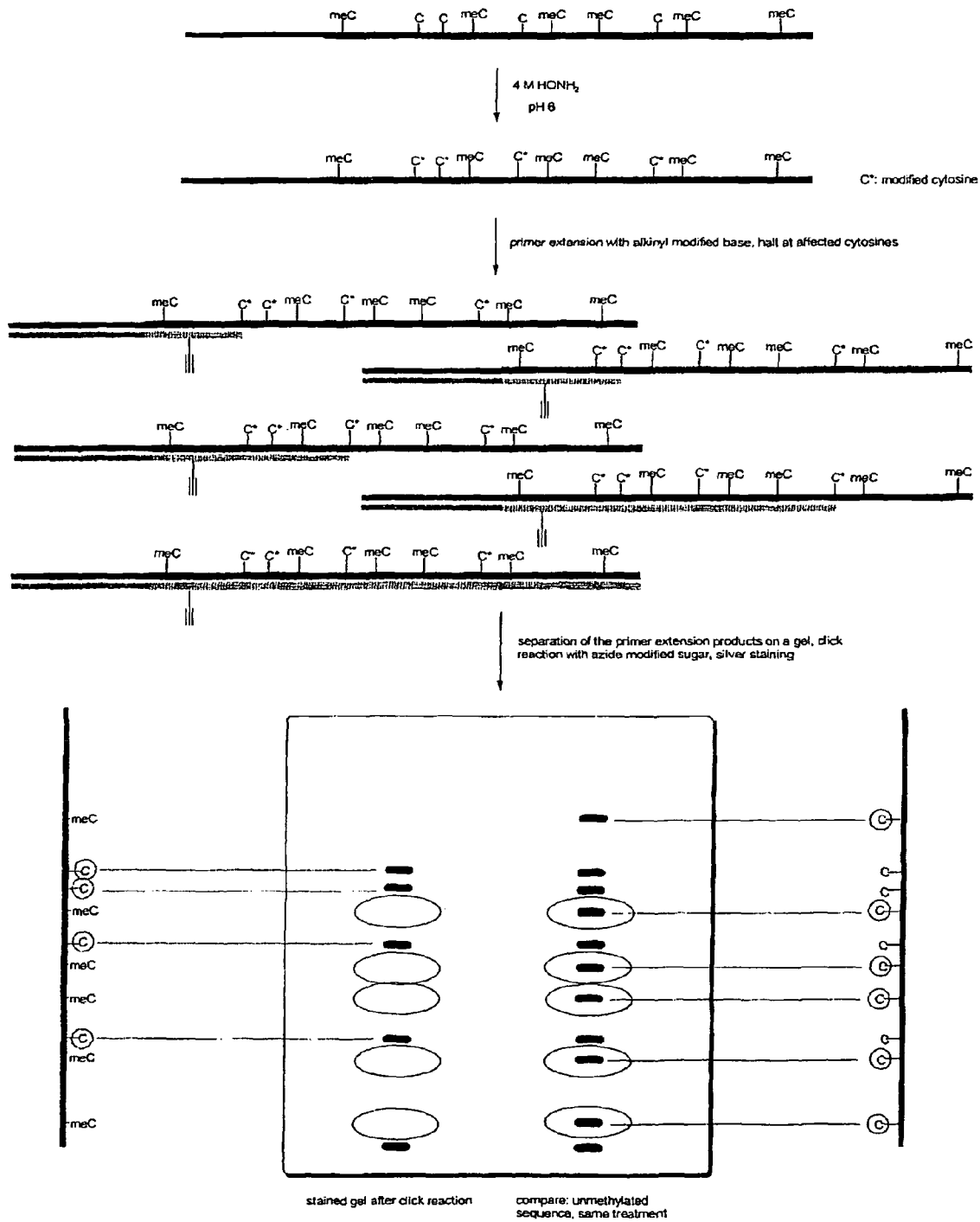

FIG. 26: Schematic depiction of a method for identifying methylation patterns in DNA by cytosine-specific chemical modifications. A DNA analyte is reacted with a cytosine (or methylcytosine) specific modification agent, e.g. hydroxylamine, preferably in a sub-stoichiometric amounts in order to give partially modified cytosine residues (C*). A primer extension reaction with an alkynyl-modified base is carried out. This reaction terminates at modified cytosine residues resulting in a "ladder" of extension products having a characteristic length. After separating the primer extension products e.g. on a gel, a Click reaction with an azide-modified marker group, e.g. a modified sugar and a subsequent detection of the marker group (e.g. via silver staining) is carried out. The methylation pattern of the DNA sample may be determined by comparing extension products from a methylated DNA sample with the extension products from an unmethylated DNA sample which has been subjected to the same treatment.

Figure 27:
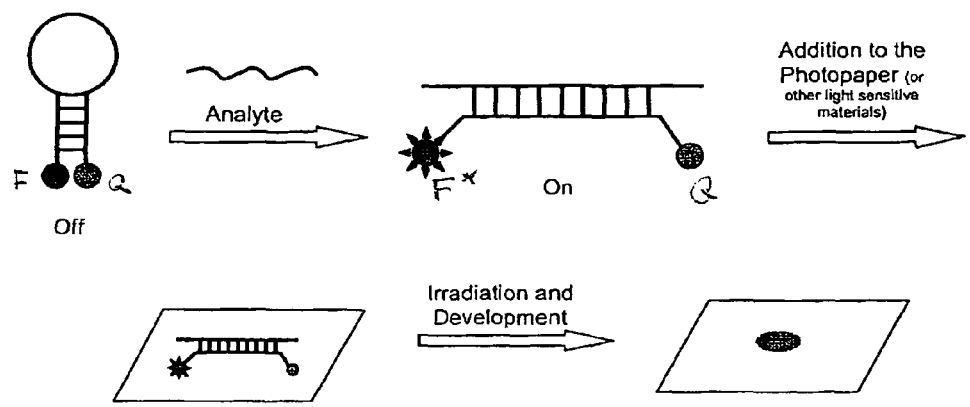

FIG. 27: Schematic depiction of a molecular beacon detection method on a photosensitive medium. A reporter molecule having a fluorescence group (F) and a quenching group (Q) is provided. In the absence of analyte, the reporter molecule has a hairpin structure and the fluorescence is quenched. In the presence of analyte the quenching group is removed from the fluorescence group which becomes unquenchend (F*). The sample is irradiated in the presence of a photographic medium such as photographic paper or other light-sensitive material and developed.

EXAMPLES

Example 1

Synthesis of Aldehyde-modified Nucleosides and Nucleotides

Nucleosides and nucleoside triphosphates with aldehyde-modified nucleobases were synthesized from appropriately modified nucleosides which carry a leaving group such as 1, preferably either on position 5 of pyrimidine bases, e.g. T, U and C or on position 7 of purine bases, e.g. 7-desaza G, 7-desaza A, G and A as shown in FIG. 1. All modifications on these positions protrude out of the DNA major groove.

Figure 2:
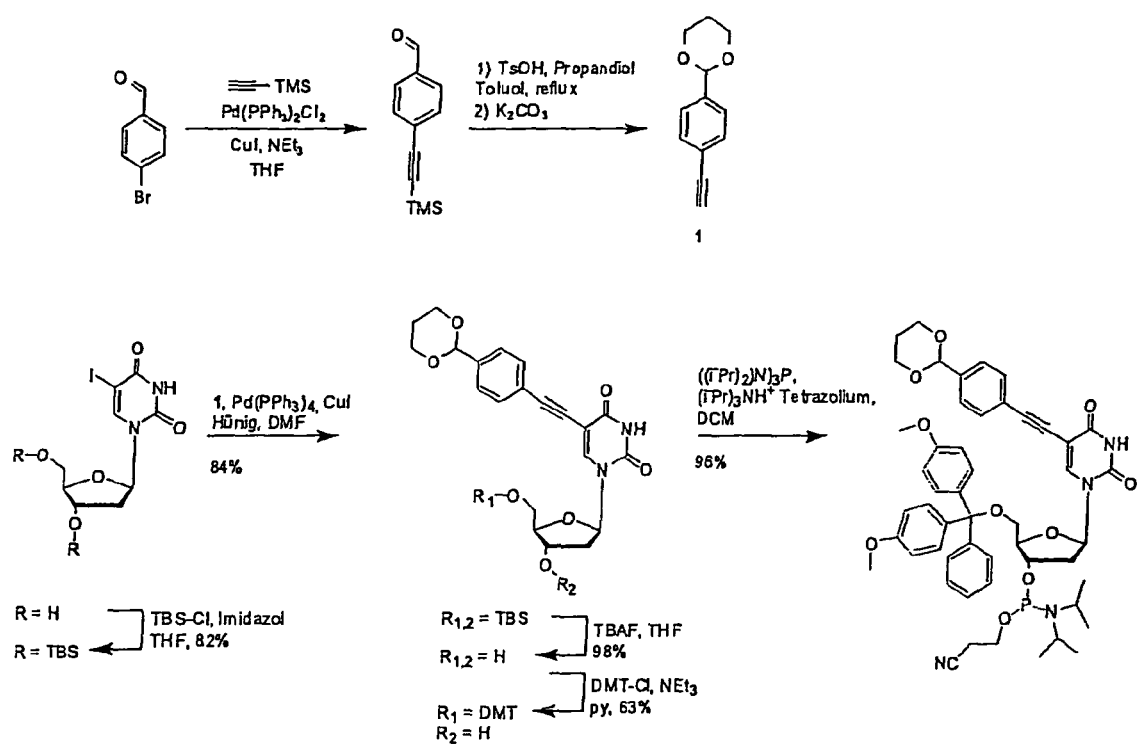
FIG. 2: Schematic representation of the synthesis of aldehyde functionalized nucleoside building blocks for the solid phase synthesis of nucleic acids.

The synthesis of an aldehyde-modified T (U) nucleoside phosphoramidite first via Sonogashira mediated alkynylation [20] followed by reaction with appropriate functional groups was performed as shown in FIG. 2. The aldehyde function was kept protected as an acetal group. The acetal protection group may be removed by treatment with acid. The modified nucleoside phosphoramidite may be incorporated into nucleic acids by chemical synthesis.

Figure 3A:
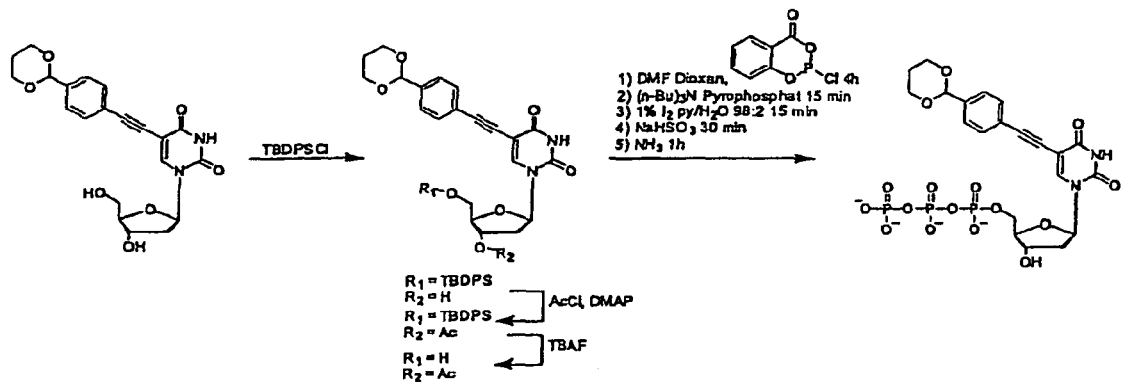
FIG. 3a: Schematic representation of the synthesis of an acetal (protected aldehyde) functionalized nucleoside triphosphate for the enzymatic synthesis of nucleic acids.
Figure 3B:
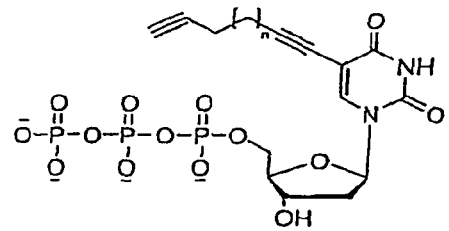
FIG. 3b: An example of an alkyne functionalized nucleoside triphosphate for efficient Click chemistry in DNA, wherein n is preferably 0-4.

The synthesis of an acetal-modified nucleoside triphosphate was carried out as shown in FIG. 3a. Further alkyne (for Click reaction), acetal- and hemiacetal-modified nucleoside triphosphates are shown in FIG. 3b. The modified nucleoside triphosphates may be incorporated into nucleic acids by enzymatic synthesis.

The use of Pd-based C—C forming reactions such as by Sonogashira/Suzuki [20] provides a general synthetic approach for the synthesis of aldehyde-modified nucleosides and nucleotides with different aldehyde groups with different modified nucleobases. Further, aldehyde groups with different steric, electronic and functional characteristics may be synthesized.

Example 2

Incorporation of Aldehyde-modified Nucleosides and Nucleotides into Oligonucleotides 2.1 Incorporation by Chemical Synthesis Incorporation of the acetal/aldehyde-modified nucleoside phosphoramidite was achieved by conventional solid phase synthesis [21]. Several DNA oligonucleotides containing one or multiple acetal/aldehyde-modified nucleobases were prepared as depicted in Table 1. Deprotection of the acetal groups afforded the aldehyde-modified DNA oligonucleotide.

The oligonucleotides were tested for their ability to form base pairs with complementary DNA strands in order to obtain double stranded DNA molecules. It was found that the reduction of duplex stability due to the presence of the aldehyde group is low. The melting point of double strands is lowered by about only 2° C. per modification. This amount of destabilisation is, however, fully acceptable for the intended applications.

TABLE 1

Oligodesoxynucleotides synthesised by solid phase synthesis.

|   |                  | Tm [° C.] |                         |
|---|------------------|-----------|-------------------------|
| 1 | TTTTTTXTTTTT     |           |                         |
| 2 | TTTTTTXXTTTTT    |           |                         |
| 3 | GCCGAXGCGC       | 53.8      | (56.5 unmodified control) |
| 4 | GCGXATAXATAXTCGC | 48.4      | (53.7 unmodified control) |
| 5 | TTXTTXTTXTTXTTX  |           |                         |

2.2 Incorporation by Enzymatic Methods

Figure 3C:
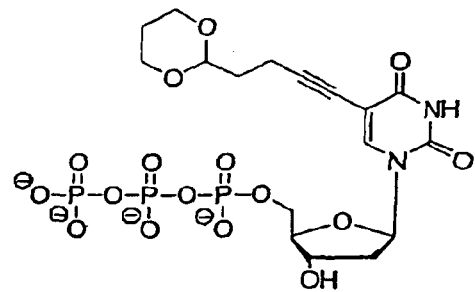
FIG. 3c: An example of a protected aldehyde functionalized triphosphate. The compounds shown in FIG. 3 are suitable for efficient PCR incorporation into DNA.

Acetal modified triphosphate monomers were prepared according to FIG. 3. The most selective method of synthesising triphosphates is the procedure following Ludwig and Eckstein [11, 12]. This procedure is slightly acidic so one obtains a mixture of aldehyde and acetal-TTP which can be separated by HPLC, if desired [13].

Studies were performed with both the acetal and aldehyde triphosphates and a variety of different DNA polymerases. They showed that all polymerases accept the modified triphosphate as substrate and they selectively incorporate the modified base. Also multiple incorporations turned out to be unproblematic. The following polymerases were tested in primer extension studies and PCR. The experiments were performed with the acetal protected thymidine and also with the deprotected aldehyde functionalized thymidine.

| Primer extention  | PCR      |
|-------------------|----------|
| Therminator (NEB) | Pfx (A)  |
| Vent              | Taq (A)  |
| Vent (exo⁻)       | Vent (B) |
| Taq               |          |

We also performed PCR studies with TPP replaced by the synthetic triphosphates (acetal and aldehyde). The PCR experiment showed that the modified base can be incorporated into a whole gene 2400 base pairs long establishing that we can create genes specifically labelled with hundreds of aldehyde derived nucleation sites.

Example 3

Detection of the Labelled Oligonucleotides and Genes

A preferred method for the metal deposition on aldehydes is based on the Tollens test [14].

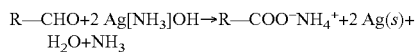

In this reaction a silver-ammonium complex is reduced by the aldehyde. If the concentration of the aldehyde is high, one can see a film of solid silver on the inside of the reaction tube.

Figure 4:
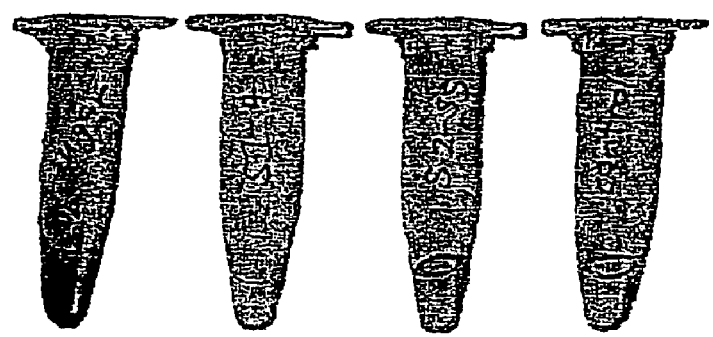
FIG. 4: The results of a metallization reaction by contacting Tollens reagent with an aldehyde-modified base: (1) sugar solution as reference, (2) DNA with one aldehyde-modified group, (3) DNA with two aldehyde groups and (4) unmodified DNA.

Both the aldehyde containing nucleoside and the chemically synthesised aldehyde-modified nucleic acids could be detected in a silver staining test indicative of aldehyde functions (FIG. 4). An unlabeled DNA strand gave in contrast a clearly negative result under the same conditions, showing that the aldehyde selectively introduced into specific DNA sequences allow selective detection of these modified sequences.

Detection of aldehyde-modified nucleic acids by silver staining was also carried out on gels. The aldehyde groups on the DNA were sufficient to reduce the silver ions within a gel. The seeds formed by the process on the DNA could be developed until a clear black band made up from deposited silver can be seen on the gel.

Figure 5:
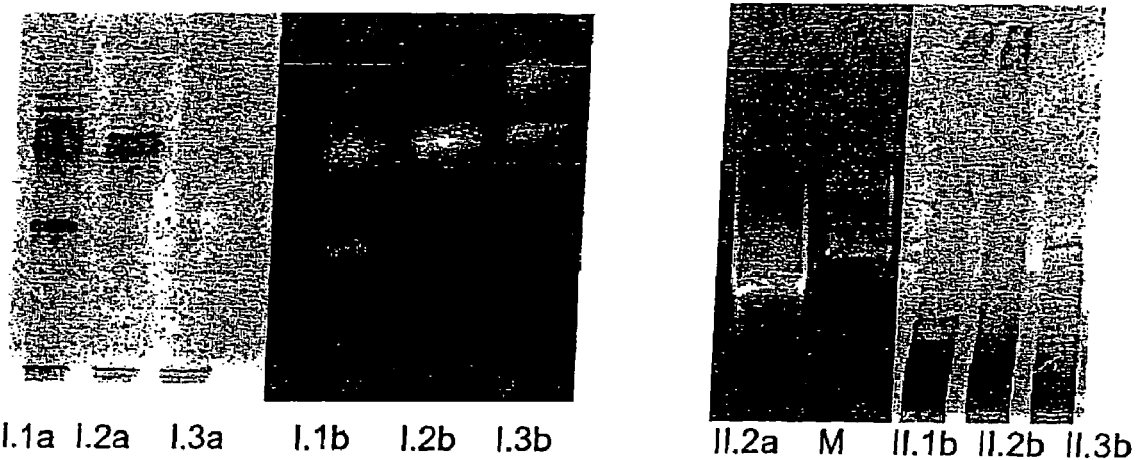
FIG. 5: (1) Primer extension products stained with Ag (a) or using a standard fluorescence dye (b): I.1a: aldehyde-modified TTP in primer extension. I.1b: acetal-modified TTP in primer extension. I.3a: unmodified DNA. Silver staining only positive on Lane 1 and 2. II1b-3b same gel but stained unspecifically with a fluorescence dye. (II) A 2142 bp PCR product stained with a fluorescent dye (a) or with Ag (b): II2a: acetal-modified TTP in PCR. M: marker; II1b: aldehyde-modified TTP in PCR, 2: acetal-modified TTP in PCR, II3b: unmodified DNA.

This was demonstrated by staining aldehyde-modified nucleic acids from primer extension reactions and from PCR (FIG. 5 (I) and (II) respectively).

As shown in FIG. 5, the DNA containing the modified nucleoside is exclusively Ag-stained while unmodified DNA stays unstained. This is true for the extended primer and for the PCR product. The staining procedure is based on the SilverXPress kit (Invitrogen), but with a stronger Tollens solution. Staining following other procedures is also possible.

Example 4

Determination of Sensitivity

Figure 6:
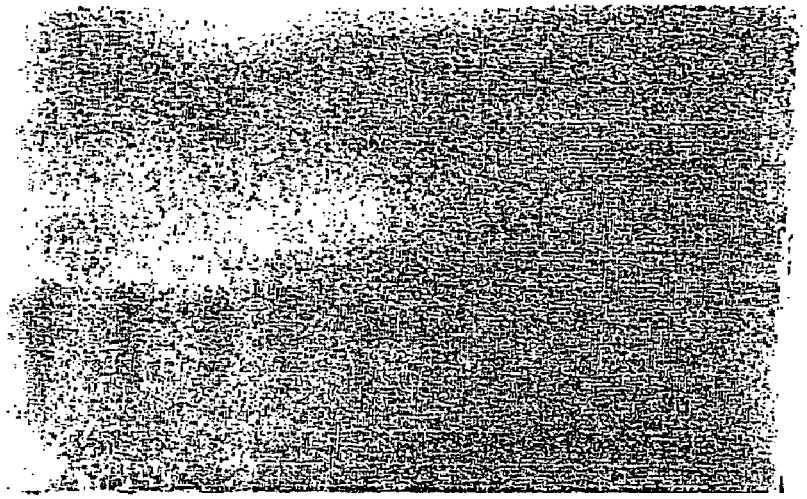
FIG. 6: The results of a dilution series with a synthetic DNA molecule containing a single aldehyde functional group. Detection by Ag-staining.
Figure 7:
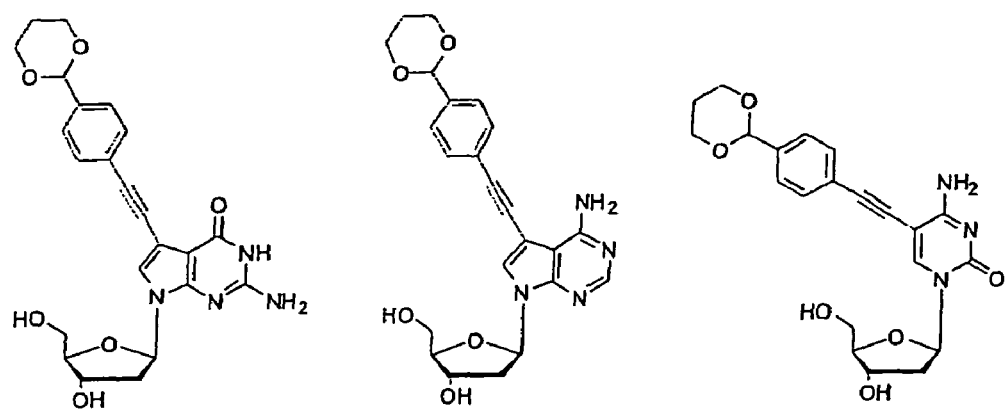
FIG. 7: Examples of nucleosides with different nucleobases carrying acetal (protected aldehyde) functions, which can be converted into corresponding phosphoramidites, H-phosphonates or triesters for chemical synthesis of nucleic acids or into 5'-triphosphates for enzymatic incorporate of nucleic acids.
Figure 8:
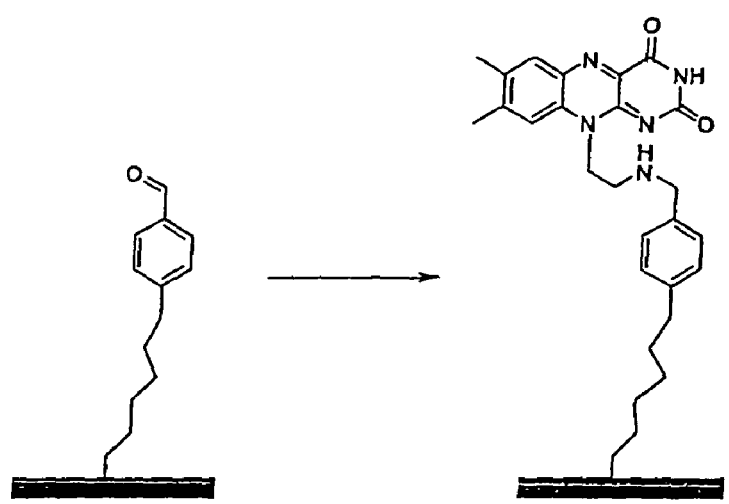
FIG. 8: Derivatisation of aldehyde modified DNA or PNA with a fluorescence tag as an alternative to metallization via reductive amination.

In order to determine the sensitivity of the detection method, dilution experiments were performed (FIG. 6). It was found that staining of aldehyde-functionalized DNA with a standard Ag staining kit was at least five times more sensitive than staining with ethidium bromide (~0.5 ng of DNA with a length of 50 bp).

This very impressive sensitivity is obtained even with coarse visual detection.

Example 5

Synthesis of Azide- and Alkyne-modified Nucleosides and Nucleotides

Nucleosides and nucleoside triphosphate with azide and alkyne-modified bases were synthesized substantially as described in Example 1.

5.1 Synthesis of Alkyne-modified Nucleotides

Figure 10:
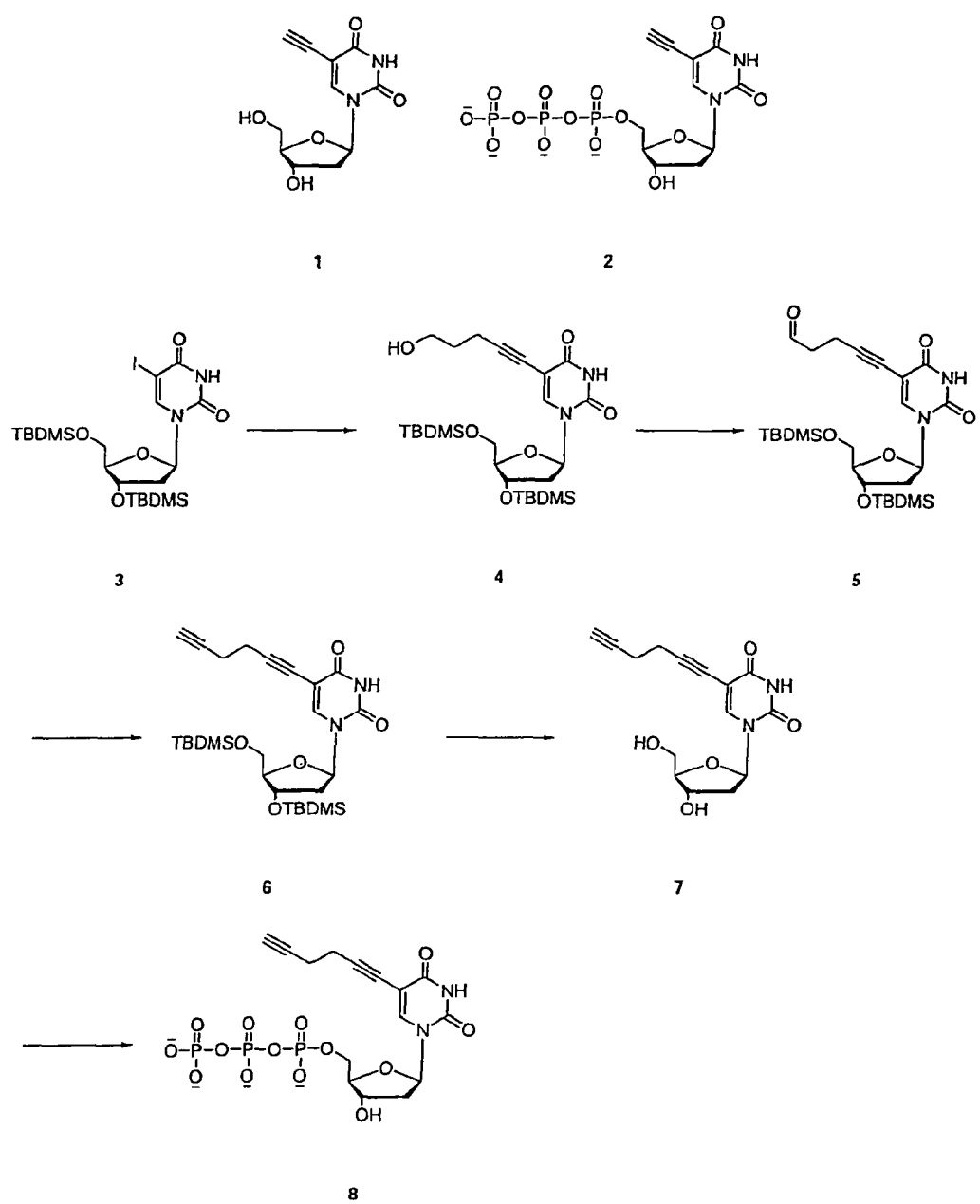
FIG. 10: Schematic representation of the synthesis of alkyne-functionalized nucleosides and nucleotide triphosphates.

A detailed reaction scheme for the synthesis of alkyne-modified nucleoside triphosphate is shown in FIG. 10.

The preparation of nucleoside (1) and its corresponding triphosphate (2) was carried out as previously [23, 24].

To a thoroughly degassed solution of 3 (1.00 g, 1.72 mmol.),[3] Pd(PPh$_3$)$_4$ (0.198 g, 0.172 mmol.) and CuI (0.065 g, 0.344 mmol.) in DMF (3 mL) was added degassed N,N-diisopropylethyl amine (1.5 mL, 8.59 mmol.) and the reaction mixture stirred at room temperature for 10 minutes. A degassed solution of 4-pentyn-1-ol (320 µL, 3.44 mmol.) in DMF (1 mL) was added dropwise to the reaction mixture over 1 hour. After complete addition, the reaction mixture was stirred at room temperature overnight. After concentration in vacuo, the crude mixture was diluted with ethyl acetate (200 mL) and the organic layer was washed with brine (3×50 mL) followed by water (50 mL). The organic layer was dried (MgSO$_4$), filtered and concentrated in vacuo. Flash column chromatography (SiO$_2$) eluting with a gradient of ethyl acetate:isohexane (1:1) followed by ethyl acetate:isohexane (2:1) provided 4 (0.790 g, 86%) as a pale yellow foam. $^1$H NMR (CDCl$_3$, 300 MHz): δ 0.01 (s, 3 H, OSiCH$_3$), 0.00 (s, 3 H, OSiCH$_3$), 0.05 (s, 3 H, OSiCH$_3$), 0.07 (s, 3 H, OSiCH$_3$), 0.81 (s, 6 H, OSi (CH$_3$)$_3$), 0.85 (s, 6 H, OSi(CH$_3$)$_3$), 1.74 (m, 2 H, CH$_2$—CH$_2$CH$_2$—OH), 1.95 (m, 1H, H-2β), 2.20 (m, 1H, H-2α), 2.42 (t, 2 H, J=6.0 Hz, C≡C—CH$_2$CH$_2$—), 3.67 (dd, 1H, J=11.4, 2.1 (CDCl$_3$, 75.5 MHz): δ 5.4 (SiCH$_3$), −5.3 (SiCH$_3$), −4.8 (SiCH$_3$), −4.6 (SiCH$_3$), 16.7 (C≡C—CH$_2$CH$_2$), 18.0 (SiC(CH$_3$)$_3$), 18.5 (SiC(CH$_3$)$_3$), 26.1 (SiC (CH$_3$)$_3$), 26.4 (SiC(CH$_3$)$_3$), 31.5 (CH$_2$—CH$_2$—CH$_2$—OH), 42.3 (C-2'), 61.9 (CH$_2$—CH$_2$CH$_2$—OH), 63.3 (C-5'), 72.4 (C≡C), 72.7 (C-3'), 86.0 (C-1'), 88.7 (C-4'), 95.0 (C≡C), 100.9 (C-5), 101.0 (C≡C), 141.9 (C-6), 149.6 (C-2), 162.4 (C-4). HRMS (ESI, +ve) calcd. for C$_{26}$H$_{46}$N$_2$NaO$_6$Si$_2$ 561.2792 [M+Na]$^+$ found 561.2803.

To a stirred solution of 4 (0.300 g, 0.56 mmol.) in dichloromethane (5 mL) was added a solution of Dess-Martin periodinane (0.378 g, 0.89 mmol.) in dichloromethane (5 mL) dropwise over 5 minutes at room temperature under a nitrogen atmosphere. The reaction mixture was stirred for 2 hours followed by quenching with saturated sodium thiosulfate solution (10 mL). The crude mixture was then diluted with dichloromethane (200 mL) and the organic layer washed with brine (2×30 mL) and water (2×30 mL). The organic layer was then dried (MgSO$_4$), filtered and concentrated in vacuo. Column chromatography (flash silica) eluting with 35% ethylacetate in isohexane afforded 5 (0.193 g, 65%) as a pale yellow foam. $^1$H NMR (CDCl$_3$, 600 MHz): δ0.07 (s, 3 H, OSiCH$_3$), 0.00 (s, 3 H, OSiCH$_3$), 0.05 (s, 3 H, OSiCH$_3$), 0.06 (s, 3 H, OSiCH$_3$), 0.81 (s, 6 H, OSi(CH$_3$)$_3$), 0.85 (s, 6 H, OSi(CH$_3$)$_3$), 1.95 (m, 1H, H-2β), 2.21 (m, 1H, H-2α), 2.61 (t, 2 H, J=7.2 Hz, —CH$_2$CH$_2$—), 2.67 (t, 2 H, J=7.2 Hz, —CH$_2$CH$_2$—), 3.68 d(d, 1 H, J=11.4, 2.4 Hz, H-5'), 3.81 (dd, 1 H, J=11.4, 2.4 Hz, H-5'), 3.89 (m, 1 H, H-4'), 4.32 (m, 1 H, H-3'), 6.20 (dd, 1 H, J=7.2, 6 Hz, H-1'), 7.84 (s, 1 H, H-6), 8.99 (bs, 1 H, N—H), 9.72 (s, 1 H, CHO). $^{13}$C NMR (CDCl$_3$, 150.8 MHz): δ3.8 (SiCH$_3$), −3.7 (SiCH$_3$), −3.1 (SiCH$_3$), −2.9 (SiCH$_3$), 14.4 (C≡C—CH$_2$CH$_2$), 19.7 (SiC(CH$_3$)$_3$), 20.1 (SiC (CH$_3$)$_3$), 27.4 (SiC(CH$_3$)$_3$), 27.7 (SiC(CH$_3$)$_3$), 43.7 (C-2'), 44.1 (CH$_2$—CH$_2$—CHO), 64.6 (C-5'), 74.0 (C-3' and C≡C), 87.5 (C-1'), 90.0 (C-4'), 94.3 (C≡C), 101.9 (C-5), 143.8 (C-6), 150.9 (C-2), 163.7 (C-4), 201.6 (CHO). HRMS (ESI, +ve) calcd. for C$_{26}$H$_{44}$N$_2$NaO$_6$Si$_2$ 559.2635 [M+Na]$^+$ found 559.2634.

To a solution of 5 (0.530 g, 1.00 mmol.) and K$_2$CO$_3$ (0.269 g, 1.98 mmol.) in dry methanol (20 mL) was added a solution of 1-diazo-2-oxo-propyl-phosphonic acid dimethyl ester (0.261 g, 1.19 mmol.) in dry methanol (5 mL) at room temperature under a nitrogen atmosphere. The reaction mixture was stirred at room temperature overnight, filtered and concentrated in vacuo. The crude mixture was dissolved in ethyl acetate (200 mL) and the organic layer was washed with brine (2×30 mL) and water (2×30 mL), dried (MgSO$_4$) and concentrated in vacuo. Column chromatography (flash silica) eluting with 20% ethylacetate in isohexane afforded 6 (0.290 g, 55%) as a colourless foam. $^1$H NMR (CDCl$_3$, 600 Mhz): δ 0.00 (s, 3 H, OSiCH$_3$), 0.01 (s, 3 H, OSiCH$_3$), 0.06 (s, 3 H, OSiCH$_3$), 0.07 (s, 3 H, OSiCH$_3$), 0.82 (s, 6 H, OSi (CH$_3$)$_3$), 0.86 (s, 6 H, OSi(CH$_3$)$_3$), 1.93 (m, 1H, H-2β), 1.95 (s, 1 H, C≡C—H), 2.22 (m, 1H, H-2α), 2.39 (dt, 2 H, J=8.4, 2.4 Hz, —CH$_2$CH$_2$—), 2.55 (t, 2 H, J=8.4 Hz, —CH$_2$CH$_2$—), 3.68 (dd, 1 H, J=11.4, 2.4 Hz, H-5'), 3.81 (d, 1 H, J=11.4, 2.4 Hz, H-5'), 3.89 (m, 1 H, H-4'), 4.33 (m, 1 H, H-3'), 6.20 (dd, 1 H, J=7.8, 6 Hz, H-1'), 7.85 (s, 1 H, H-6), 8.33 (bs, 1 H, N—H). $^{13}$C NMR (CDCl$_3$, 150.8 MHz): δ7.0 (SiCH$_3$), −6.9 (SiCH$_3$), −6.4 (SiCH$_3$), −6.2 (SiCH$_3$), 16.5 (C≡C—CH$_2$CH$_2$), 16.9 (C≡C—CH$_2$CH$_2$), 17.0 (SiC(CH$_3$)$_3$), 18.2 (SiC(CH$_3$)$_3$), 24.2 (SiC(CH$_3$)$_3$), 24.5 (SiC(CH$_3$)$_3$), 40.4 (C-2'), 61.4 (C-5'), 67.9 (C≡C—H), 70.8 (C-3'), 70.9 (C≡C), 80.9 (C≡C), 84.1 (C-1'), 86.8 (C-4'), 91.2 (C≡C), 98.7 (C-5), 140.6 (C-6), 147.5 (C-2), 159.9 (C-4). HRMS (FAB, +ve) calcd. for C$_{27}$H$_{43}$N$_2$O$_5$Si$_2$+H 533.28670 [M+H]$^+$ found 533.26009.

To a cooled solution (0° C.) of 6 (0.270, 0.51 mmol.) in THF (5 mL) was added TBAF (1.0 M, 1.52 mL, 1.52 mmol.) under a nitrogen atmosphere. The reaction mixture was stirred for 3 hours, quenched with glacial acetic acid (1.0 mL) and concentrated in vacuo. Column chromatography (flash silica) eluting with 10% methanol in ethyl acetate afforded 7 (0.127 g, 82%) as a colourless oil. $^1$H NMR (d$_6$-DMSO, 400 MHz): δ1.88 (s, 1 H, C≡C—H), 2.07 (m, 2 H, H-2'), 2.36 (dt, 2 H, J=7.2, 2.4 Hz, —CH$_2$CH$_2$—), 2.54 (t, 2 H, J=6.8 Hz, —CH$_2$CH$_2$—), 3.53 (dd, 1 H, J=12.0, 4.0 Hz, H-5'), 3.58 (dd, 1 H, J=12.0, 4.0 Hz, H-5'), 3.76 (m, 1 H, H-4'), 4.19 (m, 1 H, H-3'), 5.07 (bs, 1 H, O—H), 5.23 (bs, 1 H, O—H), 6.08 (t, 1 H, J=6.4 Hz, H-1'), 8.11 (s, 1 H, H-6), 11.55 (bs, 1 H, N—H). $^{13}$C NMR (CDCl$_3$, 150.8 MHz): δ 17.6 (C≡C—CH$_2$CH$_2$), 18.9 (C≡C—CH$_2$CH$_2$), 39.5 (C-2'), 60.7 (C-5'), 70.0 (C-3'), 73.7 (C≡C—H), 75.1 (C≡C), 84.6 (C-1'), 87.3 (C-4'), 89.1 (C≡C), 93.0 (C≡C), 100.2 (C-5), 144.7 (C-6), 151.0 (C-2), 163.2 (C-4). HRMS (FAB, +ve) calcd. for C$_{15}$H$_{16}$N$_2$O$_5$+Na [M+Na]$^+$ 327.28771 found 327.09635. HRMS (FT-ICR MS −) calcd. for C$_{15}$H$_{16}$N$_2$O$_5$+AcO$^-$ [M+AcO$^-$]$^-$ 363, 1198 found 363, 1221, MS-MS calcd. for C$_{15}$H$_{15}$N$_2$O$_5^-$ [M$^-$] 1303, 1 found 303, 1.

To a cooled solution (0° C.) of 7 (0.060 g, 0.197 mmol.) and 1,8-bis (dimethylamino)naphthalene (proton sponge, 0.068 g, 0.316 mmol.) trimethyl phosphate (2 mL) was added phosphorous oxychloride (22 µL, 0.237 mmol.) dropwise over 5 min. under a nitrogen atmosphere. The reaction mixture was stirred for 3 hours at 0° C. A solution of tributylammonium pyrophosphate (0.080 g, 0.237 mmol.) in dry DMF (2.0 mL) was added to the reaction mixture and stirred for 1 min. followed by quenching with triethylammonium bicarbonate (1.0 M, 20 mL, pH=8.5). The reaction mixture was stirred for 2 h and lyophilised overnight. RP-HPLC purification (0-50% 0.1 M triethylammonium acetate ~20: 80H$_2$O: MeCN with 0.1 M triethylammonium acetate gradient over 45 min. at a flow rate of 5 mL.min.$^{-1}$) yielded 8 (17.7 min.) as the triethylammonium salt. $^{31}$P NMR (D$_2$O, 81 MHz): δ 22.4 (t, 1 P, J=19.8 Hz, P-β), −10.5 (d, 1 P, J=20.3 Hz, P-α), −9.7 (d, 1 P, J=19.8 Hz, P-γ). MALDI-TOF (ATT matrix, negative mode): 271 [M+2H]$^{2-}$, 542 [M+2H]$^-$.

5.2 Synthesis of Dendrimeric Azide-functionalized Click Reactions Partners

Figure 11:
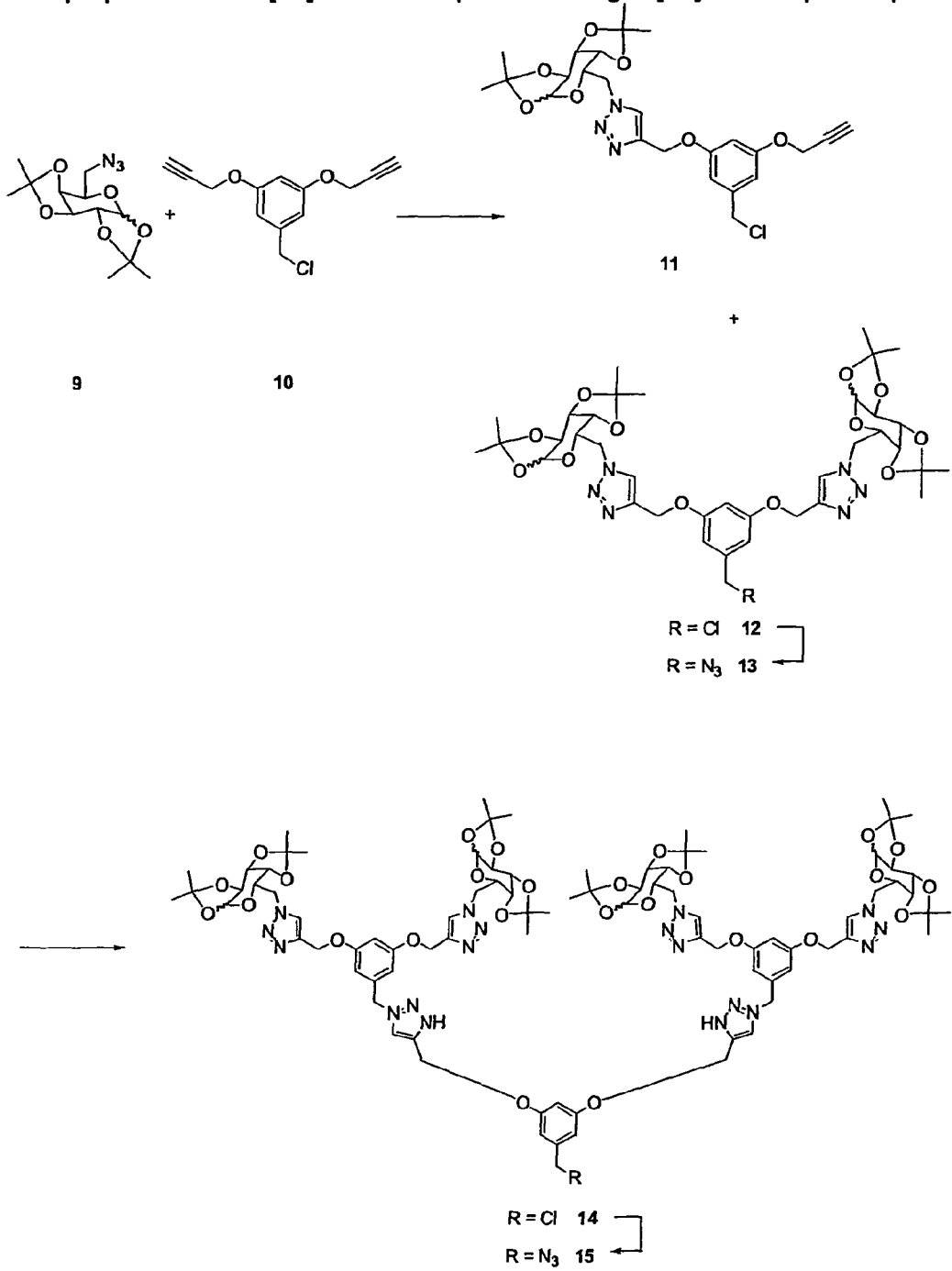
FIG. 11: Schematic representation of the synthesis of azide-functionalized dendrimers comprising protected aldehyde groups.

A detailed reaction scheme for the synthesis of azide-functionalized dendrimers containing a plurality of hemiacetal groups (protected aldehyde groups) is shown in FIG. 11.

General Procedure for the Cu(I)-catalysed Triazole Ligation Reaction

To a solution of 9 (7.31 g, 0.0256 mol.), 10 (3.00 g, 0.0128 mol.) in THF: H$_2$O (3: 1, 40 mL) was added a solution of CuSO$_4$ (0.103 g, 0.641 mmol.) in H$_2$O (3 mL) followed by solid sodium ascorbate (0.253 g, 1.28 mmol.). The reaction mixture was stirred overnight at room temperature. The suspension was diluted with H$_2$O (50 mL), cooled to 0° C. and treated with concentrated NH$_4$OH (5 mL) for 10 minutes. The reaction mixture was diluted with dichloromethane (500 mL) and the organic layer washed with brine (2×50 mL), followed by H$_2$O (2×50 mL). The organic layer was retained, dried (MgSO$_4$) and concentrated in vacuo. Column chromatography (flash silica) eluting with 1:1 ethyl acetate:petroleum spirit afforded 9 (2.76 g), mono-Click product (11, 3.94 g) as a colourless foam, followed by 12 (4.92 g, 48%). The mono-click product (11) was then reacted with one equivalent of 9 to afford 12 quantitatively after workup and with no further purification required.

$^1$H NMR (CDCl$_3$, 600 MHz): δ 1.29 (s, 6 H, C—CH$_3$), 1.35 (s, 6 H, C—CH$_3$), 1.38 (s, 6 H, C—CH$_3$), 1.49 (s, 6 H, C—CH$_3$), 4.19 (m, 4 H, H4'/H5'), 4.32 (dd, 2 H, J=4.8, 2.4 Hz, H 2'), 4.46 (dd, 2 H, J=14.4, 8.4 Hz, H6"), 4.50 (s, 2 H, —CH$_2$—), 4.62 (m, 2 H, H 3'), 4.64 (m, 2 H, H 6'), 5.18 (s, 4 H, —CH$_2$—), 5.51 (d, 2 H, J=4.8 Hz, H 1'), 6.59 (t, 1 H, J=1.8 Hz, Ar—H), 6.64 (d, 2 H, J=1.8 Hz, Ar—H), 7.79 (s, 2 H, C≡CH—). $^{13}$C NMR (CDCl$_3$, 150.8 Mhz): δ 24.4 (C—CH$_3$), 24.7 (C—CH$_3$), 25.9 (C—CH$_3$), 26.0 (C—CH$_3$), 46.1 (CH$_2$—), 50.6 (—CH$_6$'/H$_6$"), 62.2 (Ar—CH$_2$—), 67.0 (CH4'), 70.1 (CH2'), 70.5 (CH3'), 70.9 (CH5'), 96.0 (CH1'), 102.0 (Ar—CH), 107.9, 109.1, 110.0, 124.0 (C≡CH), 139.6, 143.4, 160.0. ESI-MS m/z 806 [M+H]$^+$.

The reaction of 13 (1.53 g, 1.88 mmol.) and 10 (0.220 g, 0.94 mmol.) in the presence of CuSO$_4$ (0.008 g, 0.047 mmol.) and sodium ascorbate (0.019 g, 0.094 mmol.) afforded 14 (1.65 g, 95%) as a colourless foam after column chromatography (flash SiO$_2$; ethyl acetate: methanol 9:1). $^1$H NMR (CDCl$_3$, 600 MHz): δ 1.26 (s, 12 H, C—CH$_3$), 1.27 (s, 6 H, C—CH$_3$), 1.34 (s, 12 H, C—CH$_3$), 1.35 (s, 12 H, C—CH$_3$), 1.48 (s, 6 H, C—CH$_3$), 4.19 (m, 8 H, H4'/H5'), 4.32 (m, 4 H, H 2'), 4.46 (m, 4 H, H6"), 4.47 (s, 2 H, —CH$_2$—), 4.62 (m, 4 H, H 3'), 4.64 (m, 4 H, H6'), 5.12 (s, 8 H, —CH$_2$—), 5.15 (s, 4 H, —CH$_2$—), 5.40 (s, 4 H, —CH$_2$—), 5.49 (bd, 4 H, J=4.8 Hz, H 1'), 6.50 (m, 4 H, Ar—H), 6.55 (m, 2 H, Ar—H), 6.58 (m, 1 H, Ar—H), 6.61 (m, 2 H, Ar—H), 7.59 (s, 2H, C≡CH—), 7.78 (s, 4 H, C≡CH—). $^{13}$C NMR (CDCl$_3$, 150.8 MHz): δ 24.4 (C—CH$_3$), 24.9 (C—CH$_3$), 25.9 (C—CH$_3$), 26.0 (C—CH$_3$), 45.9 (CH$_2$—), 50.4 (—CH6'/H6"), 53.9 (Ar—CH$_2$—), 61.8 (Ar—CH$_2$—), 61.9 (Ar—CH$_2$—), 67.0 (CH4'), 70.1 (CH2'), 70.5 (CH3'), 71.1 (CH5'), 96.1 (CH1'), 101.6, 101.7, 107.2, 108.0, 109.0, 109.9, 122.9, 124.2, 136.7, 140.0, 143.2, 144.1, 159.5, 160.0. MALDI-TOF (ATT, positive mode): m/z 1859 [M+H]$^+$.

General Procedure for the Conversion of Dendritic Chlorides to Azides

To a solution of 12 (4.84 g, 6.01 mmol.) in acetone:water (4:1, 100 mL) was added NaN$_3$ (0.586 g, 9.01 mmol.) and heated to reflux under a nitrogen atmosphere for 3 hours. The reaction mixture was diluted with ethyl acetate (600 mL) and the organic layer washed with brine (2×50 mL) followed by water (2×50 mL). The organic layer was retained, dried (MgSO$_4$) and concentrated in vacuo to yield 13 (4.72 g, 97%) as a white amorphous solid.

$^1$H NMR (d$_6$-acetone, 400 MHz): δ 1.28 (s, 6 H, C—CH$_3$), 1.35 (s, 6 H, C—CH$_3$), 1.36 (s, 6 H, C—CH$_3$), 1.44 (s, 6 H, C—CH$_3$), 4.30 (dd, 2 H, J=3.6, 2.0 Hz, H 6'/6"), 4.32 (d, 2 H, J=3.2, 1.6 Hz, H 5'), 4.36 (dd, 2 H, J=7.6, 1.6 Hz, H 4'), 4.39 (dd, 2 H, J=4.8, 2.4 Hz, H 2'), 4.61 (d, 2 H, J=3.6 Hz, H 6'/6"), 4.64 (s, 2 H, —CH$_2$—), 4.70 (dd, 2 H, J=7.6, 2.4 Hz, H 3'), 5.20 (s, 4 H, —CH$_2$—), 5.47 (d, 2 H, J=4.8 Hz, H1'), 6.73 (m, 3 H, Ar—H), 8.07 (s, 2 H, C≡C—H).

$^{13}$C NMR (d$_6$-acetone, 150.8 MHz): δ 25.7 (C—CH$_3$), 26.1 (C—CH$_3$), 27.2 (C—CH$_3$), 27.4 (C—CH$_3$), 47.6 (CH$_2$—), 52.0 (—CH6'/H6"), 63.4 (Ar—CH$_2$—), 68.8

(CH4'), 72.0 (CH2'), 72.5 (CH3'), 72.9 (CH5'), 98.2 (CH1'), 103.3 (Ar—CH), 109.9 (Ar—CH), 110.4, 111.2, 126.3 (C≡CH), 141.9, 144.8, 161.8. HRMS (ESI, +ve) calcd for $C_{37}H_{49}N_9O_{12}Na$ 834.3398 $[M+Na]^+$ found 834.3404.

The reaction of 14 (1.51 g, 0.81 mmol.) and $NaN_3$ (0.079 g, 1.22 mmol.) afforded 15 (1.45 g, 96%) as a white amorphous solid. $^1$H NMR ($CDCl_3$, 600 MHz): δ1.27 (s, 12 H, C—$CH_3$), 1.34 (s, 12 H, C—$CH_3$), 1.37 (s, 12 H, C—$CH_3$), 1.48 (s, 12 H, C—$CH_3$), 4.19 (m, 8 H, H4'/H5'), 4.24 (s, 2 H, —$CH_2$—), 4.32 (m, 4 H, H 2'), 4.46 (dd, 4 H, J=13.8, 8.4 Hz, H6"), 4.62 (m, 4 H, H 3'), 4.64 (m, 4 H, H 6'), 5.12 (s, 4 H, —$CH_2$—), 5.18 (s, 8H, —$CH_2$—), 5.43 (s, 4 H, —$CH_2$—), 5.49 (bd, 4 H, J=4.8 Hz, H 1'), 6.50 (m, 2H, Ar—H), 6.55 (m, 4 H, Ar—H), 6.58 (m, 1 H, Ar—H), 6.60 (m, 2 H, Ar—H), 7.78 (s, 2 H, C=CH—), 7.79 (s, 4 H, C=CH—).

$^{13}$C NMR ($CDCl_3$, 150.8 MHz): δ 24.4 (C—$CH_3$), 24.8 (C—$CH_3$), 25.8 (C—$CH_3$), 25.9 (C—$CH_3$), 45.9 ($CH_2$—), 50.4 (—CH6'/H6"), 54.6 (Ar—$CH_2$—), 62.0 (Ar—$CH_2$—), 62.1 (Ar—$CH_2$—), 67.1 (CH4'), 70.3 (CH2'), 70.7 (CH3'), 71.1 (CH5'), 96.2 (CH1'), 101.7, 101.8, 107.4, 107.7, 109.0, 109.9, 124.0, 124.2, 137.8, 143.1, 143.4, 144.1, 159.7, 159.9. HRMS (ESI, +ve) calcd for $C_{87}H_{110}N_{21}O_{26}Na$ 1886.7829 $[M+Na^+H]^+$ found 1887.7862.

The resulting modified nucleic acids can be specifically labelled according to the desired application e.g. by fluorescent labelling or metal deposition.

This labelling strategy is a fast and represents extremely sensitive method for the detection of nucleic acids, nucleic acid sequences and genes even without the need for PCR amplification.

Figure 9:
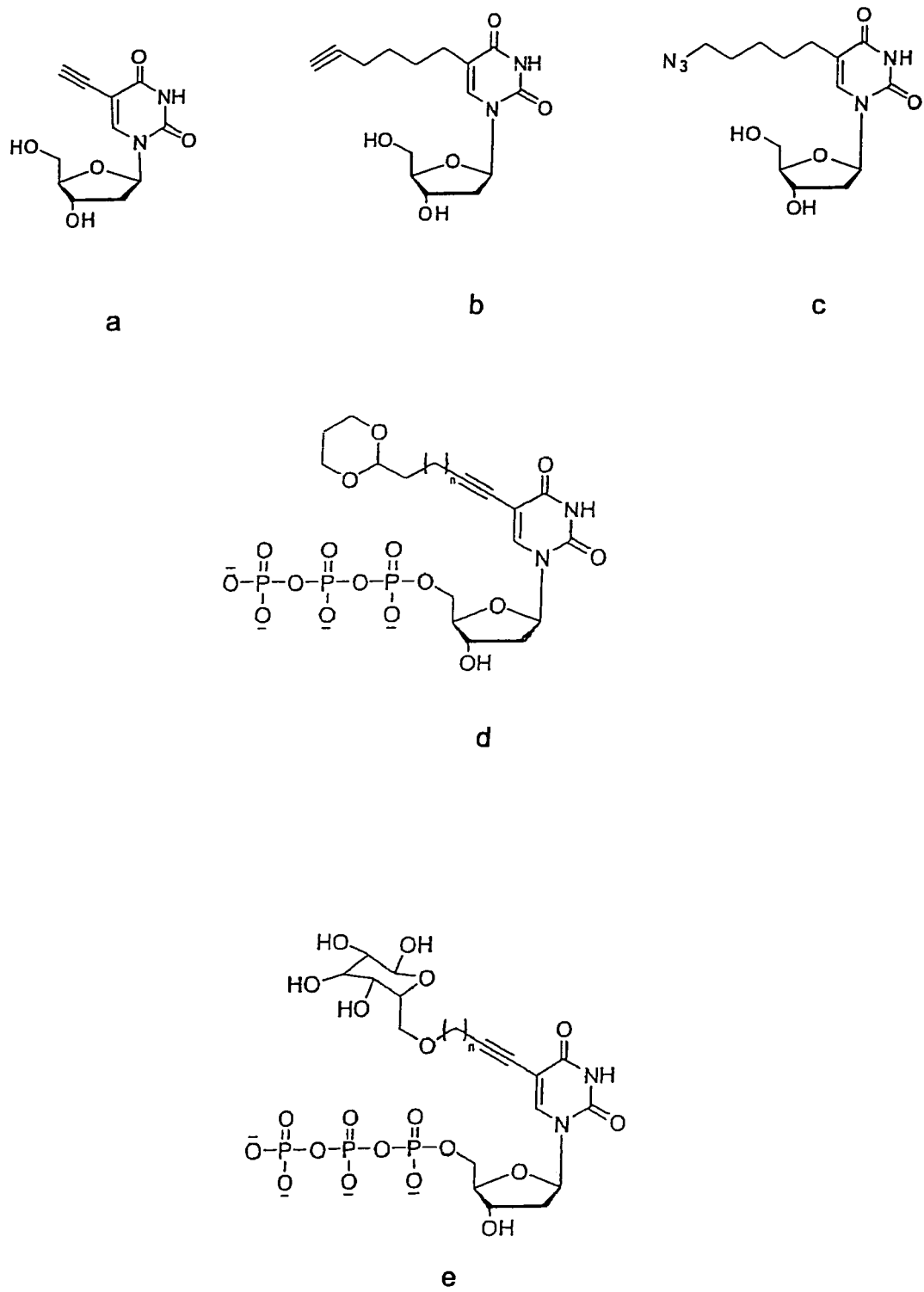
FIG. 9: Alkyne-modified (a,b), azide-modified (c) and protected aldehyde-modified (d,e) nucleoside and nucleotide monomers, wherein n is preferably 0-4.

In a first experiment, to investigate the performance of the Click reaction within a DNA architecture, the nucleosides 1 and 2 (FIGS. 9a and b) were prepared and incorporated into oligonucleotides via standard solid phase synthetic protocols. The efficiency of the Click reaction was investigated using benzyl azide, $CUSO_4$, reductant (ascorbate or TCEP) and a copper(!) stabilising ligand. The results of these are summarised in Table 2. Oligonucleotides comprising the rigid base 1 consistently afforded lower yields of the Click product compared with the flexible alkyne 2. Temperature (10 to 40° C.) did not affect yields of the Click reactions.

Figure 12:
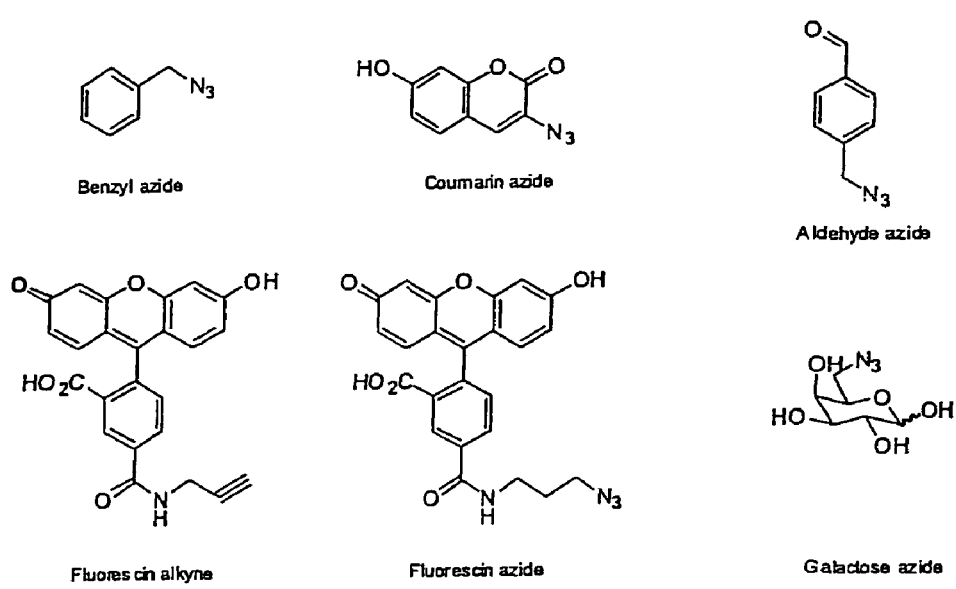
FIG. 12: Examples of azide and alkyne azide derivatives with marker or marker precursor groups for the Click reaction with alkyne- or azide-modified nucleotides or nucleic acids.

The efficiency of the Click reaction was then assayed as a function of azide type exhibiting suitable properties for detection (FIG. 12). Fluorescein azides are extremely sensitive fluorescent markers (fluorescent quantum yield almost unity), whereas the coumarin azide provides a proof of Click marker as fluorescence is switched on upon triazole formation [19].

TABLE 2

Summary of Click reactions using benzyl azide, $CuSO_4$ and TCEP.

| | X = 1 | | | X = 2 | | |
|---|---|---|---|---|---|---|
| | Yield (%) | | | | | |
| ODN sequence | Starting Material | Desired Product | Other Products | Starting Material | Desired Product | Other Products |
| 3'-GCG CTT ACX TGT CGC G-5' | 3 | 97 | — | — | 100 | Azide reduction |
| 3'-GCG CTT ACX XGT CGC G-5' | — | 84 | 16 (monoclick) | — | 100 | Azide reduction |
| 3'-GCG CTT ACX TGX CGC G-5' | — | 94 | 6 (monoclick) | — | 100 | Azide reduction |
| 3'-GCG CTX ACX TGX CGC G-5' | — | 84 | 16 (bisclick) | NA | NA | NA |

General Procedure for the Dendritic Isopropylidene Deprotection

To a mixture of TFA:water (1:1; 10 mL) was added 13 (0.020 g, 24.7 µmol.) under a nitrogen atmosphere. The reaction mixture was heated to 50° C. for 4 hours followed by concentration in vacuo. Water (20 mL) was added to the mixture and the aqueous layer was washed several times with DCM (3×20 mL), retained and lyophilized overnight to afford 16 (0.015 g, 63%) as a pale yellow foam. MALDI-TOF (ATT, positive mode): m/z 652 $[M+H]^+$.

The reaction of 15 (1.40 g, 0.75 mmol.) with TFA:water (1:1; 20 mL) afforded 17 (1.05 g, 90%) as a pale yellow amorphous solid. MALDI-TOF (ATT, positive mode): m/z 1545 $[M+H]^+$.

Example 6

Incorporating of Azide- and Alkyne-modified Nucleosides and Nucleotides into Nucleic Acids Azide- and alkyne modified nucleosides and nucleotides are efficiently incorporated into nucleic acids by chemical or enzymatic synthesis substantially as described in Example 2.

Figure 13:
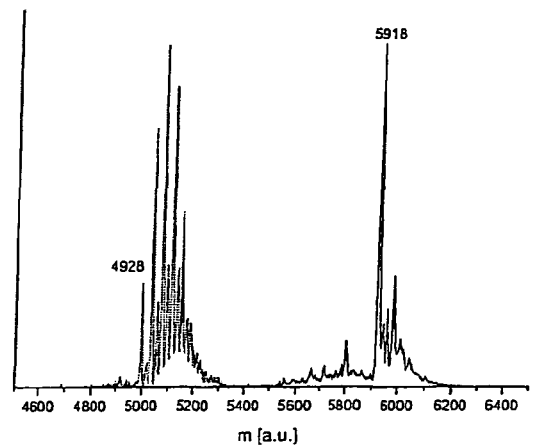
FIG. 13: On top: MALDI-TOF analysis of the Click reaction with oligonucleotides containing the modified base 2 (FIG. 9b) and fluorescein azides as the clicking partner (m: 495). Below: Gel electrophoresis of Click reactions of DNA modified with monomer 2 and fluorescine azide. A1: Fluorescence image, Lane 1: starting material prior to Click reaction; 2,3: raw reaction mixture; 4: Azide under Click conditions; A2: same gel stained with SYBR Green. B1: Lane 1,2: raw reaction mixture; 3: starting material; B2 same gel but stained with SYBR Green.
Figure 13:
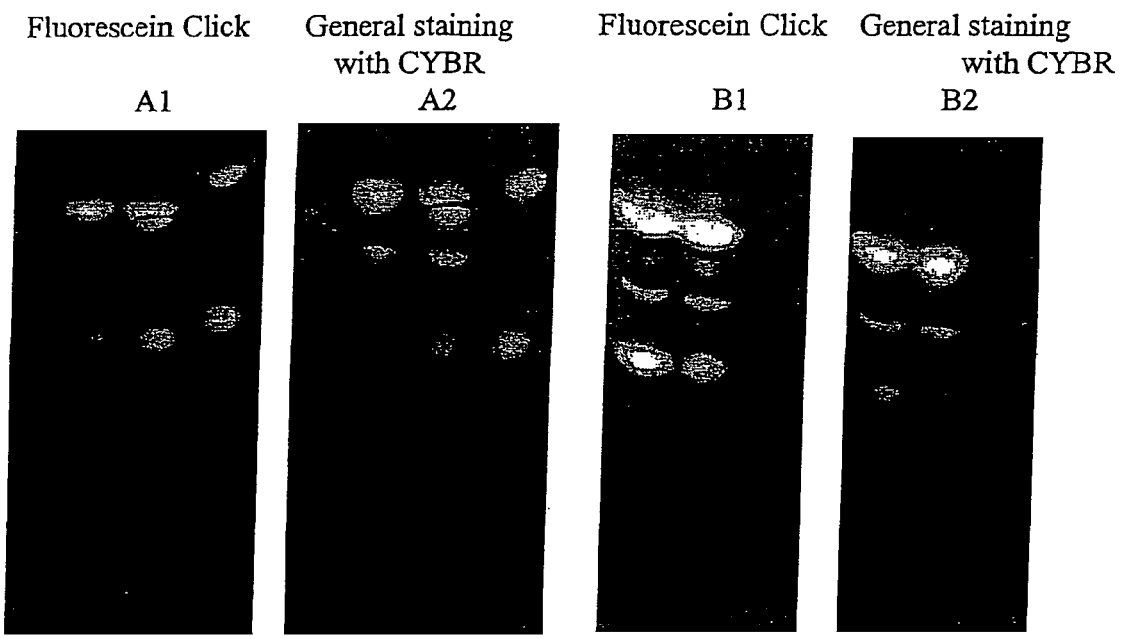

Consistent with the experiments involving the use of benzyl azide, oligodeoxy-nucleotides comprising the rigid alkyne afforded lower Click conversion yields. The flexible alkyne-containing oligonucleotides provided in contrast almost quantitative conversion according to HPLC and MALDI-TOF. Labelling of DNA was again possible directly on the gel. The DNA containing the modified nucleobase was separated from other DNA strands by gel electrophoresis and the gel was then treated with the fluorescein azide and Cu(I) to perform the Click. Washing of the gel removed excess fluorescein leaving behind the stained DNA in the gel (FIG. 13).

From these experiments is can be clearly deduced that DNA containing the alkyne modified bases can be selective labelled with fluorescein. CYBR green dyes DNA unspecifically and therefore marks also unmodified DNA prior to the click reaction as in lane 1 of A2 and lane 3 of B2 (FIG. 13).

Fluorescein is a molecule which fluoresces strongly both as a monomer and after clicking to DNA. After the click reaction with fluorescein, the gel has therefore to be washed in order to remove excess fluorescein which leaved behind the stained DNA.

Figure 14:
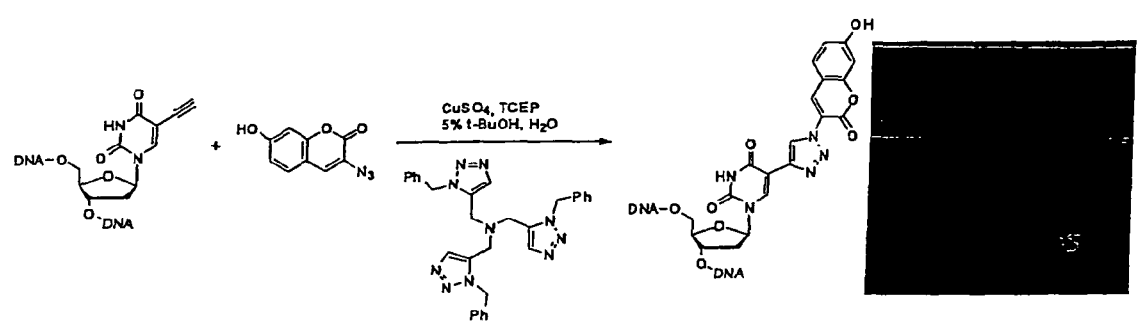
FIG. 14: Click reaction for introducing coumarin azide into DNA results in a fluorescent product (right reaction tube).

Coumarin is an alternative fluorescing molecule, which is however not fluorescing as a monomer. It starts to emit fluorescence only after the Click reaction, when the azide is converted into the triazole. The fluorescence of the coumarin switches effectively on after the click as seen in the below experiment in reaction tubes (FIG. 14). A similar experiment can be made on the gel.

Figure 15:
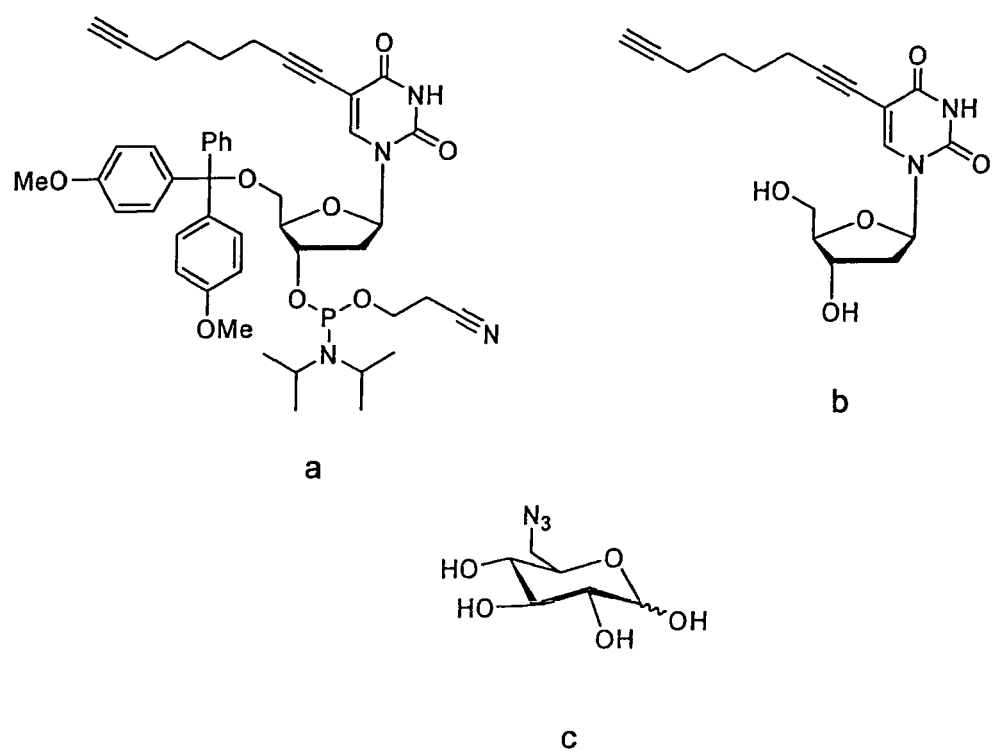
FIG. 15: An alkyne-modified phosphoramidite (a), an alkyne-modified nucleoside (b) and azide-modified galactose (c).

In a further experiment, the efficiency of the Click reaction was investigated with oligodeoxynucleotides (ODN) incorporating the nucleoside 2 (FIG. 15). This nucleoside was incorporated into oligonucleotides via standard solid phase synthetic protocols using the corresponding phosphoramidite 1 (FIG. 15). The oligonucleotides comprising a single or multiple alkyne reporter groups are shown in Table 3.

TABLE 3

ODN sequences are disclosed as SEQ ID NOS 15-17, respectively, in order of appearance.

|  | X = 19 | |
| --- | --- | --- |
|  | Mass | |
| ODN Sequences | Starting Material | Product |
| 3'-GCG CTT ACX TGT CGC G-5' | ODN1<br>4952 (calc)<br>4955 (obs) | ODN1-P<br>5157 (calc)<br>5157 (obs) |
| 3'-GCG CTT ACX XGT CGC G-5' | ODN2<br>5042 (calc)<br>5042 (obs) | ODN2-P<br>5452 (calc)<br>5455 (obs) |
| 3'-GCG CTT XXX XXX CGC G-5' | ODN6<br>5407 (calc)<br>5413 (obs) | ODN6-P<br>6637 (calc)<br>6646 (obs) |

The Click procedure involved the sequential addition of azide 3 (FIG. 15) (DMSO solution, 10 mM, 50 equiv.), $CuSO_4$/ligand[29] complex (DMSO solution, 0.05 M, 20 equiv.) and TCEP (aqueous solution, 0.1 M, 40 equiv.) solutions to a 0.2 mM solution of the corresponding ODN. The reaction mixture was shaken at room temperature overnight. The samples were then desalted by membrane and their mass determined by MALDI-TOF (HPA matrix).

Example 7

PCR Amplification of DNA Templates with Modified dNTPs)
7.1 PCR Amplification of pol η from Yeast
Template and primers employed for PCR experiments:

5'-GATTTGGGCCGGATTTGTTTC

Template: sequence of 318 bp (nt483-800 of Rad30) of yeast:

GGGCCGGATTTGTTTCAATATGCTAATGTTTGATAATGAGTACGAGCTTA

CAGGCGACTTGAAACTGAAAGATGCATTAAGCAATATTCGTGAGGCTTTT

ATAGGGGGCAACTATGATATAAATTCCCATCTACCTCTTATACCCGAAAA

GATAAAGTCTCTGAAGTTTGAAGGCGATGTTTTCAATCCAGAGGCAGAG

ATCTGATCACAGATTGGGACGATGTAATACTTGCACTAGGATCTCAGGTA

TGCAAGGGTATCAGAGATAGCATAAAAGATATTCTCGGTTATACTACTTC

GTGTGGTTTGTCTAGCAC

The 318 bp template contains 59.75% [A+T] and 40.25% [C+G].

A series of commercially available thermostabile polymerases were assessed for the ability to incorporate the modified deoxyuridine triphosphates 2 and 8 (FIG. 10) using the PCR reaction. DNA polymerases used were:
Pwo and Taq (exo$^-$) DNA polymerase (Roche)
Vent, Vent (exo$^-$), therminator polymerase (from New England Biolabs) Taq (promega).

A typical PCR reaction contained 0.05 µg genomic *S. cerevisiae* YPH 499 or 0.5 µg DNA template (pDest17-Poleta yeast[1-1889]), 0.3 mM each of the forward and reverse primers, 1.25 U polymerase and 10× polymerase buffer with magnesium, 200 µM of each unmodified dNTPs (dATP, dCTP and dGTP; NEB) and 200 µM modified dUTP. For the control were natural triphosphates (dATP, dCTP, dGTP and dTTP) used. The reactions were done in an overall volume of 50 µL. PCR experiments were performed on an Eppendorf Mastercycler Personal.

Figure 16:
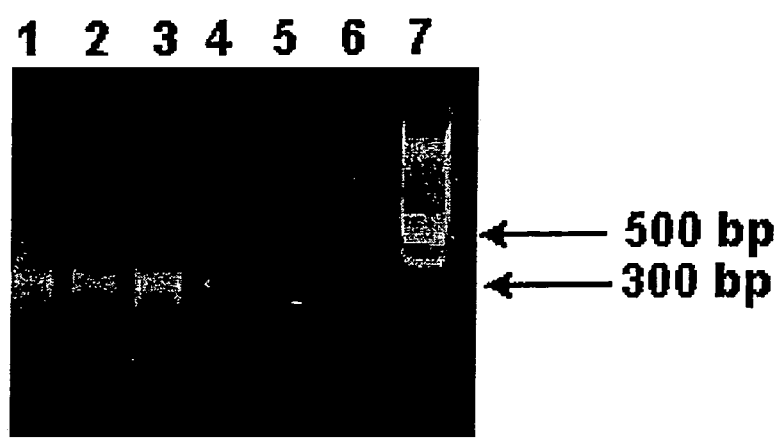
FIG. 16: PCR assay using 200 µM of 8, dATP, dCTP and dGTP, 0.05 µg genomic DNA from *S. cerevisiae* 499, 10× polymerase buffer with magnesium, 0.3 mM each of primers and 1.25 U polymerases. Lane 1) Vent, 2) Vent (exo⁻), 3) Pwo, 4) Taq (exo⁻) from Roche, 5) Therminator, 6) Taq from Promega and 7) marker.

For amplification hotstart (2 min at 94° C.) was used, followed by 10 cycles of amplification (15 sec at 94° C., 30 sec at 53° C., 45 sec at 72° C.), 25 cycles (15 sec at 94° C., 30 sec at 56° C., 45 sec at 72° C.) and a final incubation for 2 min at 72° C. PCR products were analyzed on a 2% agarose gel by staining with ethidium bromide (FIG. 16). PCR products were purified on a QIAquick PCR purification kit (Qiagen), and used for silver staining, sequencing or digestion. The products of PCR reaction were separated by 2% agarose gel electrophoresis containing ethidium bromide. The products were recorded with a Ultra-Violet Products CCD camera.

7.2 PCR Amplification of polH from Human

A typical PCR reaction contained 0.5 µg DNA template (pDest17-pIH human [1-2142], 0.3 mM each of the forward and reverse primers, 1.25 U Pwo polymerase and 10× polymerase buffer with magnesium, 200 µM of each unmodified dNTPs (dATP, dCTP and dGTP; NEB) and 200 µM modified dUTP. For the control were natural triphosphates (dATP, dCTP, dGTP and dTTP) used. The reactions were done in an overall volume of 50 µL. PCR experiments were performed on an Eppendorf Mastercycler Personal.

For amplification hotstart (2 min at 94° C.) was used, followed by 10 cycles of amplification (15 sec at 94° C., 30 sec at 53° C., 210 sec at 72° C.), 30 cycles (15 sec at 94° C., 30 sec at 56° C., 210 sec at 72° C.) and a final incubation for 7 min at 72° C. PCR products were analyzed on a 1% agarose gel by staining with ethidium bromide. PCR products were purified on a QIAquick PCR purification kit (Qiagen), and used for digestion or sequencing.

Figure 17:
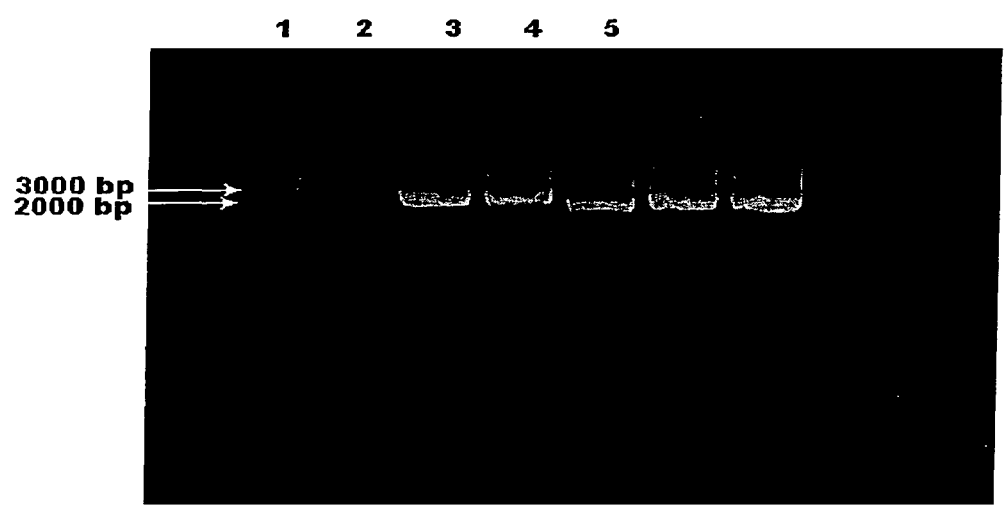
FIG. 17: PCR amplification of 2142 bp DNA with modified triphosphate 1 or 8 (FIG. 10) replacing dTTP. Agarose Gel (2%) was used and stained with Ethidium Bromide. A total of 35 PCR cycles were run, with 45 sec used for each incubation. Lane 1) NEB 2-log DNA ladder (0.1-10.0 kb), Lane 2) Negative control (minus dTTP), Lane 3) with substrate (1) replacing dTTP, 4) with substrate (8) replacing dTTP and 5) positive control (using dTTP).

The products of PCR reaction were separated by 1% agarose gel electrophoresis containing ethidium bromide. The products were recorded with a Ultra-Violet Products CCD camera. The results are shown in FIG. 17.

Figure 18:
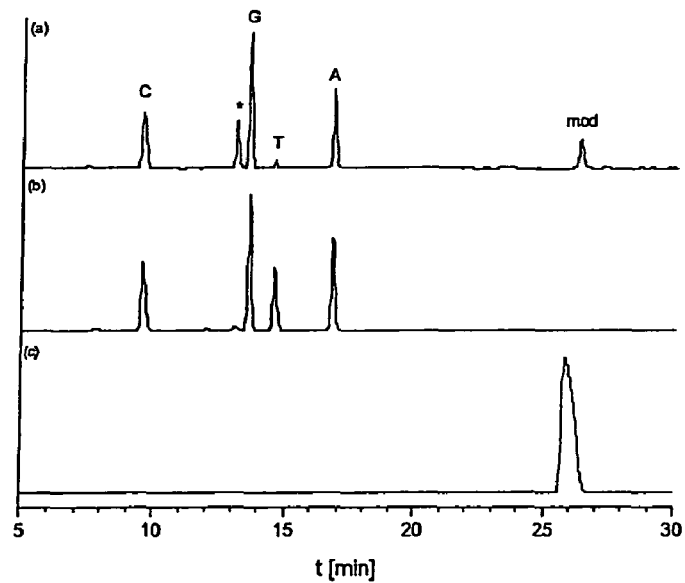
FIG. 18: HPLC chromatogram of (a) the enzymatic digest of PCR fragments (318 mer) incorporating triphosphate 8 (FIG. 10); (b) the enzymatic digest of PCR fragments incorporating dTTP; (c) nucleoside 7 (FIG. 10).
Figure 19:
FIG. 19: Dilution series of 318 bp PCR fragments incorporating triphosphates 1 and 2 followed by "on the gel" clicking and silver staining.
Figure 19:
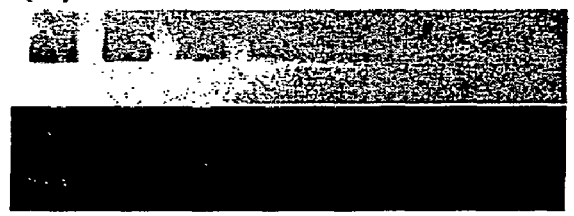
Figure 19:
Figure 19:
Figure 20A:
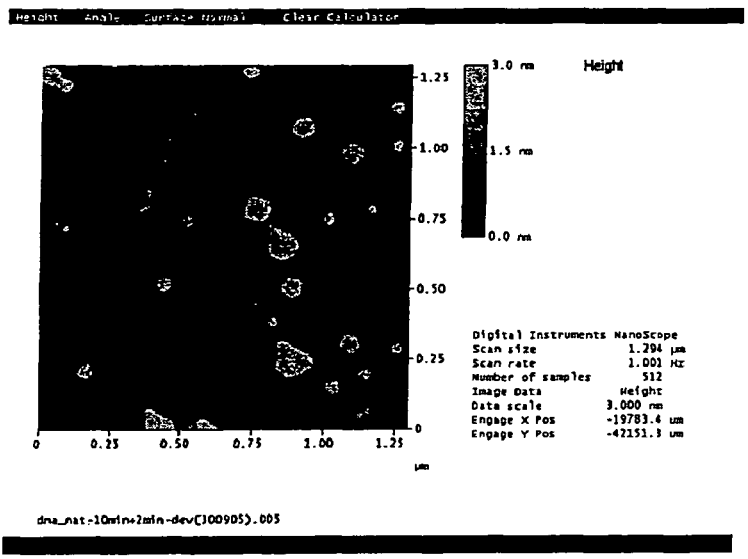
Figure 20B:
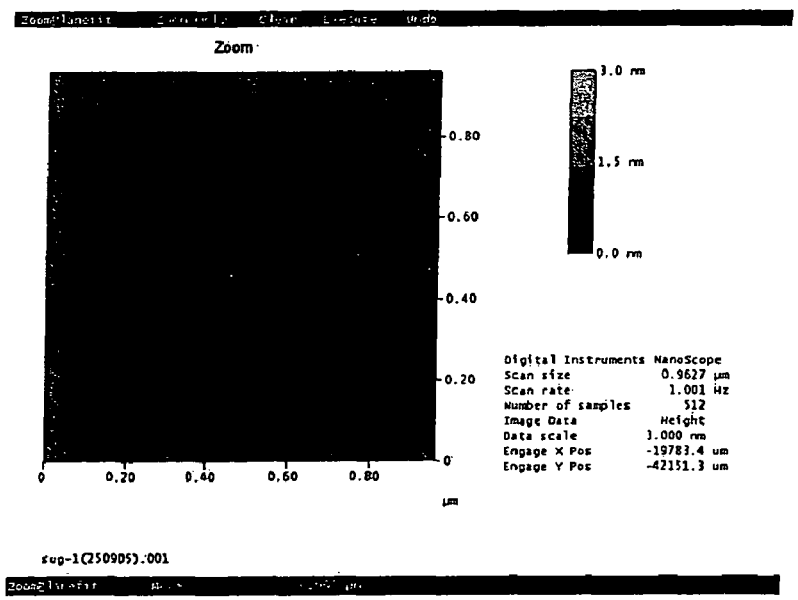
Figure 20C:
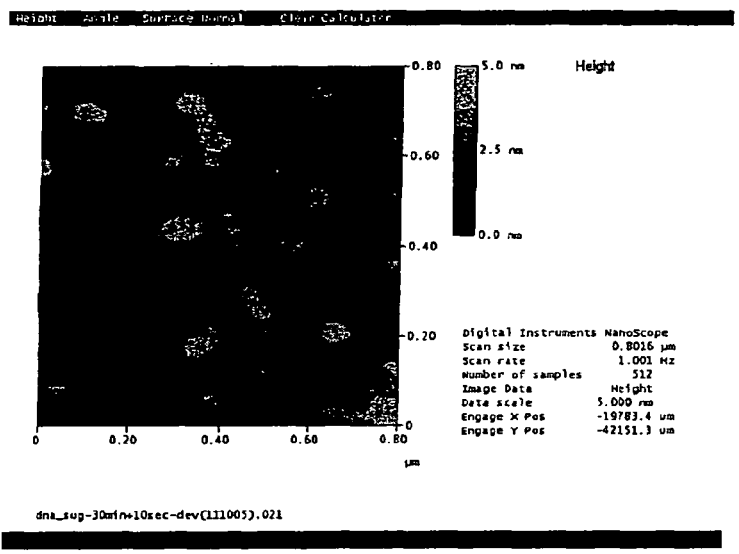
Figure 20D:
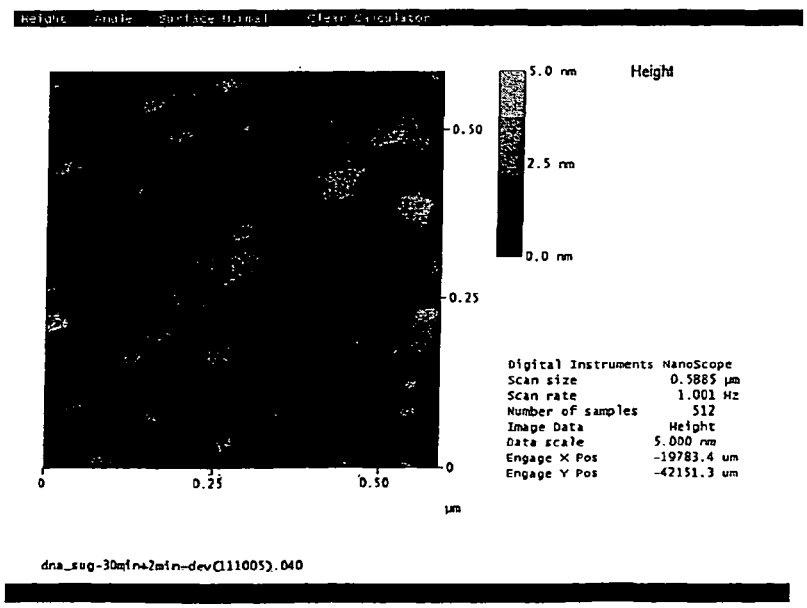
Figure 20E:
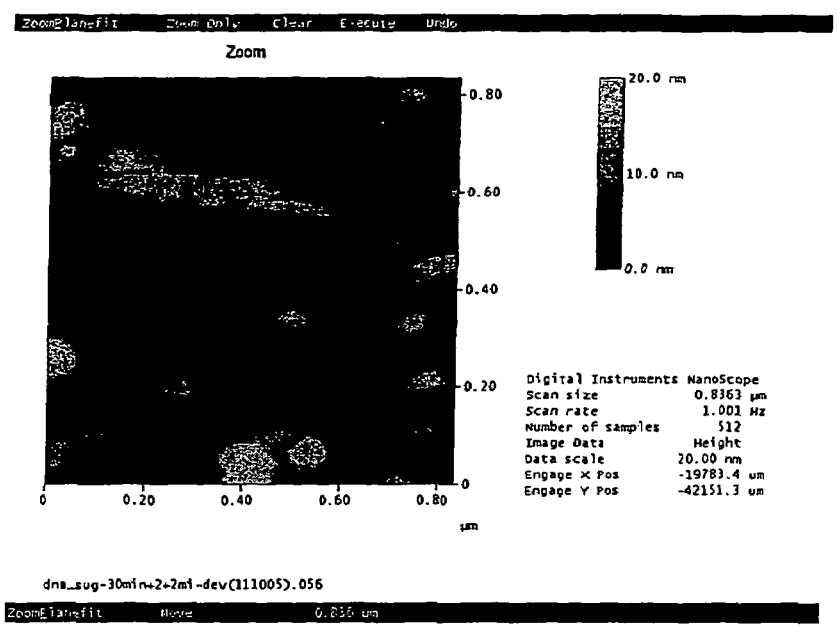

For workup 6 µL of 0.1 M HCl was added and the probes centrifuged (6000 rpm, 5 min). The digest was analysed by HPLC (interchim Interchrom Uptisphere 3 HDO column (150×2.1 mm), Buffer A: 2 mM TEA/HOAc in $H_2O$; Buffer B: 2 mM TEA/HOAc $H_2O$:MeCN 1:4; 0→30 min; 0%→30% B; 30→32 min; 30%→100% B; 32→36 min; 100% B; 36→38 min; 100%→0% B; 38→60 min; 0% B; flow 0.2 mL/min) (FIG. 18). The different peaks were assigned by co-injection, UV and FT-ICR-HPLC-MS-MS using the same conditions 7.3 Enzymatic Digestion of PCR Fragments (318 mer) Incorporating an Alkyne-mediated Nucleotide For the enzymatic digestion the 318 bp DNA template containing the modified nucleotide 8 (FIG. 10) (ca. 10 µg in 100 µL water) was incubated in 10 µL Buffer A (300 mM ammonium acetate, 100 mM $CaCl_2$, 1 mM $ZnSO_4$, pH 5.7), 22 units Nuclease P1 (Penicilinum citrium) and 0.05 unit Calf Spleen Phosphodiesterase II. The sample was shaken at 37°

C. for 3 h. The digest was completed by adding 12 µL Buffer B (500 mM Tris-HCl, 1 mM EDTA), 10 units Alkaline Phosphatase (CIP) and 0.1 unit Snake venom phosphodiesterase i (*Crotalus adamanteus venom*). The sample was shaken for another 3 h at 37° C.

7.4 General Procedure for the Cu(I)-catalysed Triazole Ligation Reaction of Sugar Azides with Modified ds DNA on Polyacrylamide Gels All click experiments were run on 318 bp PCR fragments comprising either 2 or 8 (FIG. 10) in place of dTTP. The modified PCR fragments were separated on 5% polyacrylamide gels then each gel was placed in a bath comprising 1:1 MeOH:$H_2O$ (25 mL). A solution of sugar azide (0.1 M, 3 mL) was added to the bath followed by a solution of $CuSO_4$ (0.1 M, 600 µL and finally TCEP (0.1 M, 1.2 mL). These solutions were gently shaken at room temperature overnight.

7.5 General Procedure for the Silver Staining of Sugar Azides Linked to Double-stranded DNA The click solution was decanted and each gel was washed with 1:1 MeOH: $H_2O$ (3×50 mL, 10 min. each wash), followed by $H_2O$ (3×50 mL, 10 min. each wash). Each gel was then incubated with the Tollens reagent* (40 mL) for 30 min. After subsequent washing with $H_2O$ (3×50 mL, 10 min. each wash) the gels were developed with a developing solution comprising 100 mL $H_2O$, citric acid (1%, 250 µL) and formaldehyde (35%, 80-200 µL). Depending on the formaldehyde concentration, the development process can vary from 2 min. to 20 min.

Preparation of the Tollens reagent:
To 80 mL $H_2O$ was added $AgNO_3$ (0.5 M, 5 mL), followed by NaOH (3.0 M, 1.0 mL) and finally $NH_4OH$ (1:1 conc. $NH_4OH$: $H_2O$, 2.2 mL).

Conclusion

The current invention proposed involves a new and modular method for the site specific labelling of nucleic acids by via the efficient incorporation of modified triphosphates. These modified triphosphates comprise groups that can be further functionalized, marked or stained according to the needs of the user. It is foreseeable that RNA labelling could be achieved via these methods as well using RNA polymerases and reverse transcriptase respectively. Therefore an early and efficient detection of viral genomes within a host could be effected. The reported novel nucleic acid labelling protocol is simple, efficient, sensitive and highly-selective.

Example 8

Detection of Nucleic Acids Using Photographic Processes

The black and white photographic process is one of the most sensitive chemical methods known. Photons captured on photographic paper initiate the formation of small Ag-nuclei which catalyse further silver deposition during a subsequent development process [22]. This gives rise to signal amplification factors between $10^5$ for $Ag^+$ chemical reduction and $10^{11}$ for $Ag^+$ photochemical reduction that are similar to that obtained using the PCR.

We have developed a sensitive method that utilizes photosensitizing dyes tethered to nucleic acids, which enables one to potentially detect a particular gene at subfemtomolar sensitivity (FIG. 21). This new method is simple (can use conventional photographic materials), fast (detection in minutes), efficient (only one photosensitising molecule is required per biomolecule) and sensitive (current unoptimised sensitivity levels are ~$10^{-14}$-$10^{-15}$ mol). Coupling this methodology with gene specific biochemical tools such as primer extension and PCR technologies provides a new and powerful method for the detection of nucleic acids and other analytes.

A number of fluorescent cyanine indoline (1 and 2) and quinoline dye derivatives (3) were investigated for their ability to act as photosensitizers in a photographic process (FIG. 22). The visible absorption maxima for 1-3 are 546 nm, 646 nm and 607 nm, respectively. The indoline dye (1) was readily detected down to the $3 \times 10^{-14}$ mol. (30 fmol), whereas the limit of detection of (2) was approximately 1-3 fmol (FIGS. 22a and 22b). The detection of the quinoline cyanine dye (3) was found to be more sensitive (detection limit ~0.3 fmol) than the indoline dyes (FIG. 22c). Background fog may occur upon irradiation with intense light, however, fog can be suppressed by using a low intensity infrared light source, although sensitivity is somewhat lower (FIG. 22d-f).

Figure 23:
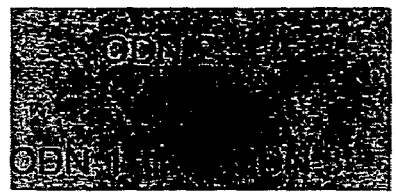
Figure 23:
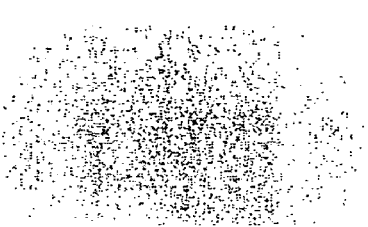

Control experiments (FIG. 23) using unmodified oligodeoxyribonucleotides (ODN-1, ODN-2, ODN-3) produced a small background negative photographic response upon high-energy irradiation at levels of 50 nmol. (i.e. three orders of magnitude difference). The negative background levels can be suppressed completely if irradiation is conducted with an infrared lamp for 5 minutes (FIG. 23b). In summary, unmodified DNA gives no staining.

A dilution series of commercially available dyes Cy5 ($\lambda_{max}$=646 nm, ODN-4) and Cy5.5 ($\lambda_{max}$=646 nm, ODN-5) tethered ODNs were then tested (FIG. 16). The detection limit of ODN-4 was found to be 100 fmol, whereas the sensitivity of Cy5.5 ODN-5 detection was a factor of ten higher (detection limit 10 fmol). Therefore, although a slight decrease in sensitivity was observed with cyanine dye conjugated ODNs compared with their non-tethered controls (FIG. 24), the results clearly demonstrate that the photography of photosensitizer-conjugated biomolecules such as ODNs can be used at a highly sensitive analytical tool.

Photosensitive dyes, e.g. compounds 4 or 5 also may be introduced into nucleic acids via Click chemistry (FIG. 25).

Conclusion

A photographic methodology can be coupled with photosensitized dye-nucleic acids to create a fast, simple, efficient and sensitive method for analyte, e.g. nucleic acid, detection.

Suitable examples of photosensitizer groups are quinoline-based cyanine dyes (e.g. 3) or indoline dyes (e.g. 1 or 2) as shown in FIG. 22, which offer sensitives of at least 10 fmol (1), 1 fmol (2) or 0.1 fmol (3).

Indoline-based dyes such as Cy5 and Cy5.5 tethered to oligodeoxyribonucleotides may be detected at levels of 100 fmol and 10 fmol, respectively.

Literature
[1] E. Braun, Y. Eichen, U. Sivan, G. Ben-Yoseph, *Nature* 1998, 391, 775.
[2] M. Mertig, L. C. Ciacchi, R. Seidel, W. Pompe, A. De Vita, *Nano Letters* 2002, 2, 841.
[3] J. Richter, *Physica E* 2003, 16, 157.
[4] K. Keren, M. Krueger, R. Gilad, G. Ben-Yoseph, U. Sivan, E. Braun, *Science* 2002, 297, 72.
[5] F. Patolsky, Y. Weizmann, O. Lioubashevski, I. Willner, *Angew. Chem. Int. Ed.* 2002, 41, 2323.
[6] E. Katz, I. Willner, *Angewandte Chemie-International Edition* 2004, 43, 6042.
[7] K. Keren, R. S. Berman, E. Braun, *Nano Letters* 2004, 4, 323.
[8] Y. Weizman, F. Patolsky, I. Popov, I. Willner, *Nano Letters* 2004, 4, 787.
[9] C. F. Monson, A. T. Wooolley, *Nano Letters* 2003, 3, 359.
[10] S. Brakmann, S. Lobermann, *Angewandte Chemie-International Edition* 2001, 40, 1427.
[11] K. Burgess, D. Cook, *Chemical Reviews* 2000, 100, 2047.

[12] J. Ludwig, F. Eckstein, *Journal of Organic Chemistry* 1991, 56, 1777.
[13] A. Roychowdhury, H. Illangkoon, C. L. Hendrickson, S. A. Benner, *Organic Letters* 2004, 6, 489.
[14] B. Tollens, *Chem. Ber.* 1882, 15, 1635.
[15] H. C. Kolb, M. G. Finn, K. B. Sharpless, *Angew. Chem. Int Ed.* 2001, 40, 2004.
[16] B. W. Kirk, M. Feinsod, R. Favis, R. M. Kliman, F. Barany, *Nucleic Acids Res.* 2002, 30, 3295.
[17] X.-b. Zhong, R. Reynolds, J. R. Kidd, K. K. Kidd, R. Jenison, R. A. Marlar, D. C. Ward, *PNAS* 2003, 100, 11559.
[18] A. C. Syvanen, *Nat. Rev. Genet.* 2001, 2, 930.
[19] K. Sivakumar, F. Xie, B. M. Cash, S. Long, H. N. Barnhill, Q. Wang, *Organic Letters* 2004, 6, 4603.
[20] J. D. Kahl, M. M. Greenberg, *J. Am. Chem. Soc.* 1999, 121, 598-604.
[21] R. Micura, Angew. Chem. Int. Ed. 2002, 41 813), 2265-2269.
[22] T. H. James, in *Advances in Photochemistry* Vol. 13 (Eds. D. H. Volman, K. Gollnick, G. Hammond), John Wiley & Sons New York, 1986, p. 329ff.
[23] P. J. Barr, A. S. Jones, P. Serafinowski, R. T. Walker, *J. Chem. Soc., Perk. Trans.* 1, 1978, 10, 1263.
[24] L. Otvos, J. Szecsi, J. Sagi, T. Kovacs, *Nucleic Acids Symp. Ser.* 1987, 18, 125.
[25] K. Fujimoto, S. Matsuda, N. Takahashi, I. Saito, *J. Am. Chem. Soc.* 2000, 122, 5646.
[26] F. MorisVaras, X. H. Qian, C. H. Wong, *J. Am. Chem. Soc.* 1996, 118, 7647.
[27] D. C. M. Kong, M. von Itzstein, *Carbohydrate Research* 1997, 305, 323.
[28] D. Graham, J. A. Parkinson, T. Brown, *J. Chem. Soc., Perkin Trans.* 1, 1998, 1131-1138.
[29] Q. Wang, T. R. Chan, R. Hilgraf, V. V. Fokin, K. B. Sharpless, M. G. Finn, *J. Am. Chem. Soc.* 2003, 125, 3192-3193.

The invention claimed is:

1. A method for detecting a nucleic acid analyte in a sample comprising the steps:
    (i) providing a sample;
    (ii) contacting the sample with a functionalized compound comprising at least one alkyne functional group which is a first reaction partner for a Click reaction, said Click reaction being a (3+2) cycloaddition reaction between azide and alkyne groups forming a 1,2,3-triazole ring, and wherein the functional group is attached to position 5 or 6 of a pyrimidine nucleobase or to position 7 of a 7-deazaadenine or 7-deazaguanine nucleobase or to position 8 of a purine nucleobase or an oligomer or polymer thereof, under conditions wherein said compound forms an association product which specifically binds by hybridization to the analyte to be detected or the complement thereof,
    (iii) contacting the association product with a second reaction partner for said Click reaction comprising a complementary azide group under conditions wherein a Click reaction between the first and second reaction partner occurs, wherein the second reaction partner further comprises a fluorescence marker group, and
(iv) detecting said marker group.

2. The method of claim 1, comprising a qualitative detection.

3. The method of claim 1, comprising a quantitative detection.

4. The method of claim 1, wherein the analyte to be detected is a nucleic acid selected from DNA and RNA.

5. The method of claim 1, wherein the sample is a biological sample.

6. The method of claim 5, wherein the sample is an agricultural or nutritional sample.

7. The method of claim 5, wherein the sample is a clinical sample.

8. The method of claim 1, wherein the detection is carried out directly without amplification.

9. The method of claim 1, wherein the detection is carried out in combination with an amplification step between steps (i) and (ii).

10. The method of claim 1, wherein a sequence-specific detection of a nucleic acid analyte is carried out.

11. The method of claim 10, wherein the forming of said association product comprises a sequence-specific hybridization reaction.

12. The method of claim 1, wherein the alkyne functional group is attached to the compound via a direct bond or spacer.

13. The method of claim 12, wherein said spacer is a flexible spacer or an at least partially rigid spacer.

14. The method of claim 13, wherein the spacer comprises at least one group selected from the group consisting of alkene, alkyne, cyclic groups, and combinations thereof 15. The method of claim 1, wherein said functionalized compound is selected from:
(i) a functionalized nucleic acid or nucleic acid building block and/or
(ii) a functionalized nucleic acid or nucleic acid.

16. The method of claim 15, wherein the forming of said association product comprises incorporating said functionalized building block into a nucleic acid or nucleic acid analogue molecule.

17. The method of claim 16, wherein said functionalized nucleotide or nucleotide analogue is incorporated into a nucleic acid molecule by an enzyme selected from DNA polymerase and RNA polymerase.

18. The method of claim 16, wherein the forming of said association product comprises hybridizing said functionalized nucleic acid or nucleic acid analogue to the analyte to be detected.

19. The method of claim 15, comprising a primer extension reaction optionally in combination with a nucleic acid amplification reaction.

20. The method of claim 19 comprising:
providing at least one primer molecule which hybridizes under the assay conditions with the nucleic acid analyte to be detected or the complement thereof and extending said primer, wherein at least one functionalized nucleotide or nucleotide analogue is incorporated into the extension product.

21. The method of claim 19 comprising:
providing at least one functionalized primer molecule which hybridizes under the assay conditions with the nucleic acid analyte to be detected or the complement thereof, extending said primer molecule, wherein an extended primer molecule is formed.

22. The method of claim 1, wherein the detection is carried out by optical means.

23. The method of claim 1, wherein the detection is carried out by electrical means.

24. The method of claim 1, comprising a parallel detection of a plurality of nucleic acids.

25. The method of claim 1, wherein the detection is carried out on a solid surface optionally a microarray chip.

26. The method of claim 1, wherein said sample is an agricultural sample.

27. The method of claim 26, wherein nucleic acids are detected from plants, plant pathogens or plant pests.

28. The method of claim 26, wherein genetic variabilities are detected in plants, plant pathogens or plant pests.

29. The method of claim 26, wherein herbicide, fungicide or pesticide resistances, tolerances or intolerances in fungi, insects or plants are detected.

30. The method of claim 26, wherein species or strains of fungi, insects or plants are genotyped and/or differentiated.

31. The method of claim 26, wherein genetically modified organisms or strains of fungi, insects or plants are detected and/or differentiated.

32. The method of claim 1, wherein genetic variabilities in humans are detected.

33. The method of claim 32, wherein medicament resistance, tolerance or intolerance, or allergy is detected.

34. The method of claim 32, wherein genotyping is determined.

35. The method of claim 32, wherein a genetically modified organism or strain is detected.

36. The method of claim 32, wherein genetic diseases, allergic diseases, autoimmune diseases or infectious diseases are detected.

37. The method of claim 1, wherein the function and/or expression of a gene is detected.

38. The method of claim 1, wherein specific information encoded in products is detected.

39. The method of claim 32, wherein specific information encoded in a product is detected.

40. A method for detecting a nucleic acid analyte in a sample comprising the steps:
(i) providing a sample;
(ii) contacting the sample with a functionalized compound comprising at least one alkyne functional group which is a first reaction partner for a Click reaction, said Click reaction being a (3+2) cycloaddition reaction between azide and alkyne groups forming a 1,2,3-triazole ring, and wherein the functional group is attached to position 5 or 6 of a pyrimidine nucleobase or to positions 7 or 8 of a 7-deazaadenine or 7-deazaguanine nucleobase or to position 8 of a purine nucleobase or an oligomer or polymer thereof, under conditions wherein said compound forms an association product which specifically binds by hybridization to the analyte to be detected or the complement thereof,
(iii) contacting the association product with a second reaction partner for said Click reaction comprising a complementary azide group under conditions wherein a Click reaction between the first and second reaction partner occurs, wherein the second reaction partner further comprises a fluorescence marker group, and
(iv) detecting said marker group,
wherein the (3+2) cycloaddition reaction between azide and alkyne groups is catalyzed by copper(I).

* * * * *

SEQUENCE LISTING

```
<160> NUMBER OF SEQ ID NOS: 20

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcgattcgtt cgtcgc                                                           16

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgcgaatgaa cagcgc                                                           16

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gcgaccgatt cgc                                                              13

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Cyanin5-modified g

<400> SEQUENCE: 4
```

```
gcgctgttca ttcgcg                                                      16

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Cyanin5-modified g

<400> SEQUENCE: 5
gcgctgttca ttcgcg                                                      16

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: acetal/aldehyde-modified a, c, g or t

<400> SEQUENCE: 6 tttttttnttt tt                                                         12

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: acetal/aldehyde-modified a, c, g or t

<400> SEQUENCE: 7 tttttttnntt ttt                                                        13

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: acetal/aldehyde-modified a, c, g or t

<400> SEQUENCE: 8 gccgangcgc                                                             10

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (4)..(4)
<223> OTHER INFORMATION: acetal/aldehyde-modified a, c, g or t
<220> FEATURE:
<221> NAME/KEY: modified_base
<222> LOCATION: (8)..(8)
<223> OTHER INFORMATION: acetal/aldehyde-modified a, c, g or t
<220> FEATURE:
<221> NAME/KEY: modified_base
<222> LOCATION: (12)..(12)
<223> OTHER INFORMATION: acetal/aldehyde-modified a, c, g or t

<400> SEQUENCE: 9
gcgnatanat antcgc                                                   16

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: acetal/aldehyde-modified a, c, g or t
<220> FEATURE:
<221> NAME/KEY: modified_base
<222> LOCATION: (6)..(6)
<223> OTHER INFORMATION: acetal/aldehyde-modified a, c, g or t
<220> FEATURE:
<221> NAME/KEY: modified_base
<222> LOCATION: (9)..(9)
<223> OTHER INFORMATION: acetal/aldehyde-modified a, c, g or t
<220> FEATURE:
<221> NAME/KEY: modified_base
<222> LOCATION: (12)..(12)
<223> OTHER INFORMATION: acetal/aldehyde-modified a, c, g or t
<220> FEATURE:
<221> NAME/KEY: modified_base
<222> LOCATION: (15)..(15)
<223> OTHER INFORMATION: acetal/aldehyde-modified a, c, g or t

<400> SEQUENCE: 10
ttnttnttnt tnttn                                                    15

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: acetal/aldehyde-modified a, c, g or t

<400> SEQUENCE: 11
gcgctgtnca ttcgcg                                                   16

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: acetal/aldehyde-modified a, c, g or t

<400> SEQUENCE: 12
```
gcgctgnnca ttcgcg                                                    16

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: acetal/aldehyde-modified a, c, g or t
<220> FEATURE:
<221> NAME/KEY: modified_base
<222> LOCATION: (8)..(8)
<223> OTHER INFORMATION: acetal/aldehyde-modified a, c, g or t

<400> SEQUENCE: 13
gcgcngtnca ttcgcg                                                    16

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: acetal/aldehyde-modified a, c, g or t
<220> FEATURE:
<221> NAME/KEY: modified_base
<222> LOCATION: (8)..(8)
<223> OTHER INFORMATION: acetal/aldehyde-modified a, c, g or t
<220> FEATURE:
<221> NAME/KEY: modified_base
<222> LOCATION: (11)..(11)
<223> OTHER INFORMATION: acetal/aldehyde-modified a, c, g or t

<400> SEQUENCE: 14
gcgcngtnca ntcgcg                                                    16

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: acetal/aldehyde-modified a, c, g or t

<400> SEQUENCE: 15
gcgctgtnca ttcgcg                                                    16

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: acetal/aldehyde-modified a, c, g or t

<400> SEQUENCE: 16

```
gcgctgnnca ttcgcg                                              16

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(10)
<223> OTHER INFORMATION: acetal/aldehyde-modified a, c, g or t

<400> SEQUENCE: 17
gcgcnnnnnn ttcgcg                                              16

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gatttgggcc ggatttgttt c                                        21

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gttcccatag tctctatcgt atttt                                    25

<210> SEQ ID NO 20
<211> LENGTH: 318
<212> TYPE: DNA
<213> ORGANISM: Saccharomyces cerevisiae

<400> SEQUENCE: 20
gggccggatt tgtttcaata tgctaatgtt tgataatgag tacgagctta caggcgactt    60
gaaactgaaa gatgcattaa gcaatattcg tgaggctttt ataggggggca actatgatat  120 aaattcccat ctacctctta tacccgaaaa gataaagtct ctgaagtttg aaggcgatgt  180
tttcaatcca gagggcagag atctgatcac agattgggac gatgtaatac ttgcactagg  240
atctcaggta tgcaagggta tcagagatag cataaaagat attctcggtt atactacttc  300
gtgtggtttg tctagcac                                               318
```